US011155847B2

(12) United States Patent
Madsen, II et al.

(10) Patent No.: US 11,155,847 B2
(45) Date of Patent: *Oct. 26, 2021

(54) PROCESS FOR THE PRODUCTION OF ISOMALTOOLIGOSACCHARIDES

(71) Applicants: ISOThrive LLC, Healdsburg, CA (US); Board of Supervisors of Louisiana State University and Agricultural and Mechanical College, Baton Rouge, LA (US)

(72) Inventors: Lee Madsen, II, Manassas, VA (US); Jack Oswald, Healdsburg, CA (US); Donal F Day, Baton Rouge, LA (US); Young Hwan Moon, Baton Rouge, LA (US)

(73) Assignee: ISOThrive Inc., Healdsburg, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/505,536

(22) PCT Filed: Aug. 22, 2015

(86) PCT No.: PCT/US2015/046441
§ 371 (c)(1),
(2) Date: Feb. 21, 2017

(87) PCT Pub. No.: WO2016/029198
PCT Pub. Date: Feb. 25, 2016

(65) Prior Publication Data
US 2017/0275661 A1 Sep. 28, 2017

Related U.S. Application Data

(60) Provisional application No. 62/041,006, filed on Aug. 22, 2014, provisional application No. 62/151,404, filed on Apr. 22, 2015.

(51) Int. Cl.
C12P 19/04 (2006.01)
C12P 19/08 (2006.01)
C08B 37/00 (2006.01)
C12N 9/44 (2006.01)
C12P 19/18 (2006.01)
C12N 1/20 (2006.01)
A61K 31/715 (2006.01)
C12P 19/20 (2006.01)
C12R 1/01 (2006.01)

(52) U.S. Cl.
CPC ............ C12P 19/04 (2013.01); A61K 31/715 (2013.01); C08B 37/0009 (2013.01); C12N 1/205 (2021.05); C12P 19/18 (2013.01); C12P 19/20 (2013.01); C12Y 204/01005 (2013.01); C12R 2001/01 (2021.05)

(58) Field of Classification Search
CPC ........... C12P 19/18; C12P 19/04; C12P 19/08; C12N 9/1051; C12Y 204/01005

USPC ........ 435/101, 103, 211, 252.3, 258.2, 258.3
See application file for complete search history.

(56) References Cited

U.S. PATENT DOCUMENTS

| 5,580,762 A | 12/1996 | Karube et al. |
| 2004/0149200 A1 | 8/2004 | Shimose et al. |
| 2008/0064657 A1 | 3/2008 | Day et al. |
| 2019/0093139 A1 | 3/2019 | Madsen, II et al. |

FOREIGN PATENT DOCUMENTS

| AU | 2015305276 B2 | 8/2020 |
| CN | 107249598 | 10/2017 |
| WO | 2016029198 | 2/2016 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Dols et al. Appld and Env. Microbiol. 1998, pp. 1298-1302.*
Iliev et al. J. Appld. Micro. 2008, 104, pp. 243-250.*
"International Application Serial No. PCT/US2015/046441, International Search Report dated Nov. 30, 2015", 3 pgs.
"International Application Serial No. PCT/US2015/046441, Written Opinion dated Nov. 30, 2015", 7 pgs.
"European Application Serial No. 15833983.8, Response filed Sep. 12, 2017 to Communication pursuant to Rules 161(1) and 162 EPC dated Apr. 18, 2017", 12 pgs.
"European Application Serial No. 15833983.8, Extended European Search Report dated Jun. 6, 2018", 5 pgs.
"European Application Serial No. 15833983.8, Response Filed Dec. 21, 2018 to Extended European Search Report dated Jun. 6, 2018", 9 pgs.
"Chinese Application Serial No. 201580053577.1, Office Action dated Jul. 16, 2019", with English translation, 14 pages, 2019.
"Australian Application Serial No. 2015305276, First Examination Report dated Nov. 29, 2019", 3 pgs.
"Chinese Application Serial No. 201580053577.1, Office Action dated Jan. 3, 2020", w/ English Translation, 11 pgs.
"Chinese Application Serial No. 201580053577.1, Response filed Nov. 27, 2019 to Office Action dated Jul. 16, 2019", w/ English Claims, 10 pgs.

(Continued)

Primary Examiner — Robert B Mondesi
Assistant Examiner — Mohammad Y Meah
(74) Attorney, Agent, or Firm — Schwegman Lundberg & Woessner, P.A.

(57) ABSTRACT

The present invention provides a method for the production of oligosaccharides by the fermentation of dextran-sucrase-producing microorganisms with sucrose and maltose. The disclosed process allows for the control of the final composition of the isomaltooligosaccharides by adjustments to pH and the initial ratio of sucrose to maltose.

24 Claims, 10 Drawing Sheets

(56) References Cited

OTHER PUBLICATIONS

"Australian Application Serial No. 2015305276, Response filed Apr. 21, 2020 to First Examination Report dated Nov. 29, 1", 28 pages.

"Australian Application Serial No. 2015305276, Subsequent Examiners Report dated May 15, 2020", 5 pages.

"Chinese Application Serial No. 201580053577.1, Response filed May 15, 2020 to Office Action dated Jan. 3, 2020", with English Claims, 6 pages.

Llliev, I, "Gluco-oligosaccharides synthesized by glucosyltransferases from constitutive mutants of Leuconostoc mesenteroides strain Lm 28", Journal of Applied Microbiology (2008) vol. 104, (2008), pp. 243-250.

"Chinese Application Serial No. 201580053577.1, Decision of Rejection dated Jan. 18, 2021", 10 pgs.

"European Application Serial No. 15833983.8, Communication Pursuant to Article 94(3) EPC dated Feb. 22, 2021", 6 pgs, 2021.

"Australian Application Serial No. 2015305276, Response filed Jul. 23, 2020 to Subsequent Examiners Report dated May 15, 2020", 9 pgs.

"Canadian Application Serial No. 2,969,748, Office Action dated Apr. 21, 2021", 4 pages.

"Chinese Application Serial No. 201580053577.1, Response filed Apr. 20, 2021 to Decision of Rejection dated Jan. 18, 2021", with English Claims, 10 pages.

"European Application Serial No. 15833983.8, Response filed Jun. 22, 2021 to Communication Pursuant to Article 94(3) EPC dated Feb. 22, 2021", 17 pages.

"European Application Serial No. 15833983.8, Communication Pursuant to Article 94(3) EPC dated Jun. 29, 2021", 4 pages.

* cited by examiner

FIG. 8

| pH: | Maltose: | Peak2: | Peak3: | Peak4: | Peak5. | Peak6: |
|---|---|---|---|---|---|---|
| 5.5 | 0.16 | 10.99 | 18.96 | 14.37 | 4.61 | 0.88 |
| 5.6 | -1.04 | 10.34 | 19.72 | 15.24 | 4.82 | 0.90 |
| 5.7 | -1.95 | 9.93 | 20.30 | 15.85 | 4.94 | 0.91 |
| 5.8 | -2.58 | 9.75 | 20.69 | 16.22 | 4.99 | 0.91 |
| 5.9 | -2.91 | 9.81 | 20.90 | 16.34 | 4.95 | 0.89 |
| 6 | -2.96 | 10.11 | 20.93 | 16.20 | 4.83 | 0.86 |
| 6.1 | -2.73 | 10.65 | 20.78 | 15.82 | 4.63 | 0.82 |
| 6.2 | -2.20 | 11.42 | 20.45 | 15.18 | 4.36 | 0.77 |
| 6.3 | -1.39 | 12.43 | 19.94 | 14.29 | 3.99 | 0.71 |
| 6.4 | -0.29 | 13.68 | 19.25 | 13.16 | 3.55 | 0.63 |
| 6.5 | 1.09 | 15.17 | 18.37 | 11.77 | 3.03 | 0.54 |
| 6.6 | 2.77 | 16.90 | 17.31 | 10.13 | 2.43 | 0.44 |
| 6.7 | 4.73 | 18.86 | 16.08 | 8.24 | 1.74 | 0.33 |
| 6.8 | 6.98 | 21.06 | 14.66 | 6.10 | 0.97 | 0.20 |
| Min/Max: | -2.96 | 9.75 | 20.93 | 16.34 | 4.99 | 0.91 |

PROCESS FOR THE PRODUCTION OF ISOMALTOOLIGOSACCHARIDES

CROSS-REFERENCE TO RELATED APPLICATIONS

This application is a U.S. National Stage application filed under 35 U.S.C. § 371 of International Patent Application Serial No. PCT/US2015/046441, filed Aug. 22, 2015 and published on Feb. 25, 2016 as WO 2016/029198, which claims the benefit of U.S. Provisional Application Ser. No. 62/041,006, filed Aug. 22, 2014, and of U.S. Provisional Application Ser. No. 62/151,404, filed Apr. 22, 2015, the benefit of priority of each of which is claimed hereby and each of which are incorporated by reference herein in its entirety.

BACKGROUND OF THE INVENTION

Dietary supplements, sometimes also called nutraceuticals, are either food or food constituents that purportedly provide medical or health benefits which can include prevention of disease (Stephen, D. F. L., *Trends in Food Sci. Tech*, 1995, 6:59-61). The term typically includes the following representative classes: probiotics, prebiotics, dietary fiber, omega-3fatty acids and antioxidants (Pandey, M. et al., *Asian J. Pharm. Clin. Res.*, 2010, 3:11-15). Due to increasing numbers of health conscious consumers in Asia, the United States and Europe, the dietary supplement market, specifically in the areas of oligosaccharides and prebiotics, has demonstrated significant growth over the last three decades (Goffin, D. et al., *Crit. Rev. Food. Sci. Nutr.*, 2011, 51:394-409; Roberfroid, M. B., *Br. J. Nutr.*, 2002, 88 Suppl 2:S133-8) and new, economical methods for their production are in demand.

Of interest here are the pre- and probiotic classes of dietary supplements. Broadly defined, probiotics are made up of living cultures of bacteria, such as those in yogurt, that promote the growth of healthy gut flora by means of population support (Gilliland, S. E. et al., "Health and Nutritional Properties of Probiotics in Food including Powder Milk with Live Lactic Acid Bacteria", 2001, p. 1-34, World Health Organization). Prebiotics, however, are materials, either physical (e.g. dietary fiber) or chemical (e.g. butyrate) which can promote the growth of selected beneficial flora (Chung, C. H., et al., *Poult. Sci.*, 2004, 83:1302-6) and/or exert some beneficial effect directly on intestinal epithelial cells (thus improving uptake of nutritive calories, vitamins, minerals, etc.). Because many prebiotics can overcome the resistance of the digestive barrier facilitating the proliferation and/or activity of desired populations of bacteria in situ (Gibson G. R. et al., *J. Nutr.*, 1995, 125:1401-12; Van Loo, J. et al., *Br. J. Nutr.*, 1999, 81:121-32), research and development in this area has boomed. Additionally, prebiotics are often found naturally in the food supply, especially fermented foods and are generally compatible with most food formulations (Macfarlane, S. et al., *Aliment Pharmacol. Ther.*, 2006, 24:701-14; Manning, T. S. et al., *Best Pract. Res. Clin. Gastroenterol.*, 2004, 18:287-98). By definition, glucooligosaccharides are prebiotic agents, and many forms are commercially available.

Glucooligosaccharides are a class of carbohydrate oligomers that include isomaltooligosaccharides (IMO). IMOs are glucosyl saccharides with a core structure based on an α-(1→6) linked backbone that may include α-(1→4), α-(1→3) (nigerooligosaccharides) and\or α-(1→2) (kojioligosaccharides) linked branches (Yun, J. et al., *Biotechnol. Lett.*, 1994, 16:1145-1150). These glucosidic linkages are found in commercial IMO syrups (Goffin, D. et al., *Crit. Rev. Food Sci. Nutr.*, 2011, 51:394-409.)

Chung and Day have produced glucooligosaccharides, specifically IMOs, via the action of dextransucrase generated in situ upon sucrose in the presence of a maltose acceptor (U.S. Pat. No. 7,291,607). The IMO was an extracellular product of the fermentation of sucrose by *Leuconostoc mesenteroides* ATCC® 13146™. Chung and Day demonstrated that these glucooligosaccharides (branched IMOs) are readily utilized by *bifidobacterium* sp. and *lactobacillus* sp., but not by *Escherichia coli* or *Salmonella* sp. in pure-culture studies (Chung, C. H. and Day, D. F., *J. Ind. Microbiol. Biotechnol.*, 2002, 29:196-9).

SUMMARY OF THE INVENTION

In one aspect, this invention provides a method for the preparation of oligosaccharides comprising the steps of (a) contacting a feedstock comprising a fixed ratio of sucrose to maltose with a dextransucrase-producing microorganism in an aqueous culture medium; (b) fermenting the feedstock with the bacteria cells at a pH between 4 and 8; (c) removing the bacteria cells; and (d) polishing, wherein the final composition of the oligosaccharides produced is varied according to the pH selected and the initial feedstock ratio employed. In one embodiment, performing steps (a) to (c) is continuous. In another embodiment, the method is conducted as an immobilized enzyme or an immobilized cell process. In a further embodiment, the method is conducted as a batch operation or as a fed-batch operation.

In another embodiment, the fixed ratio of sucrose to maltose ranges between the ratios 1.5:1 to 7:1. In one embodiment, the fixed ratio is maintained at 2:1 or at 2.33:1 or at 2.75:1. In a further embodiment, the fixed ratio of sucrose to maltose is adjusted during the fermentation process by the addition of either more sucrose or more maltose.

In another embodiment, the dextransucrase-producing microorganism is *Leuconostoc mesenteroides* [in particular *Leuconostoc mesenteroides* ATCC 13146 or *Leuconostoc mesenteroides* NRRL B-742 or *Leuconostoc mesenteroides* subsp. *mesenteroides* (Tsenkovskii) van Tieghem (ATCC® 11449™), or NRRL B-1299], *Leuconostoc citreum*, *Leuconostoc gasicomitatum*, or *Leuconostoc kimchii*. In a further embodiment, the dextransucrase-producing microorganism is *Weisella confusa*, *Weissella cibaria*, *Lactococcus* spp *Penicillium aculeatum*, *Pediococcus* spp (*pentosaceus*), *Streptococcus mutans*, *Streptococcus oralis*, *Streptococcus sanguinis*, or *Lactobacillis* spp (*reuteri*).

In another embodiment, the pH is controlled by adding an acid or a base to the culture medium. In a further embodiment, the base comprises an alkali earth metal hydroxide or carbonate. In one embodiment, the alkali earth metal is calcium. In another embodiment, the base comprises sodium hydroxide.

In one embodiment, the bacteria cells are removed by centrifugation, filtration or clarification. In another embodiment, the polishing removes insoluble impurities. In a further embodiment, the polishing comprises decolorization. In one embodiment, the decolorization utilizes activated charcoal or activated carbon. In a further embodiment, the decolorization comprises using a weak base anion resin. In yet another embodiment, the polishing comprises de-ashing. In one embodiment, the de-ashing comprises using a strong acid cation resin to remove metal ions. In another embodiment, the de-ashing comprises a two-step process using a strong acid followed by a weak base. In a further embodiment, the polishing comprises removing protein. In another embodiment, the removing protein comprises heating, then evaporating the aqueous culture medium followed by centrifugation or filtration. In one embodiment, the removing protein comprises using a weak base anion resin. In another embodiment, the polishing comprises removing organic acids. In one embodiment, the removing organic acids comprises utilizing a weak base anion resin. In another embodiment, the removing organic acids comprises liquid chromatography using a chromatographic grade gel-type strong acid cation exchange resin in calcium form (SAC-Ca++).

In another embodiment, the polishing comprises removing mannitol. In another embodiment, the removing the mannitol utilizes continuous or pulsed liquid chromatography. In a further embodiment the removing the mannitol utilizes evaporation followed by one or two stages of cooling to initiate crystallization and precipitation.

In another embodiment, the final composition of the oligosaccharides produced comprises isomaltooligosaccharides with one or more α-(1→4) at the reducing end and α-(1→6) linkages with a degree of polymerization between 3 and 9 or between 3 and 10. In a further embodiment, the isomaltooligosaccharides further comprise α-(1→4), α-(1→3) and/or α-(1→2) branching.

Another embodiment further comprises providing the oligosaccharides as a concentrated solution, optionally prepared under suitable conditions for human consumption. A separate embodiment further comprises providing the oligosaccharides as a powder, optionally prepared under conditions suitable for human consumption. In one embodiment, the powder is produced by drying, spray drying or by freeze drying.

In another aspect of the invention, a composition is produced by the method described above. Optionally, the composition is suitable for human consumption.

Another aspect of the invention provides for the preparation of oligosaccharides comprising the steps of contacting a feedstock comprising a fixed ratio of sucrose to maltose with a dextransucrase-producing microorganism in a culture medium; (b) fermenting the feedstock with the bacteria cells at a pH between 4 and 8; (c) removing the bacteria cells; and (d) polishing; wherein the final oligosaccharides produced are essentially free of ash, mineral acids, residual proteins, sugar alcohols, and organic acids. In one embodiment, performing steps (a) to (c) is continuous. In another embodiment, the method is conducted as an immobilized enzyme or an immobilized cell process. In a further embodiment, the method is conducted as a batch operation or as a fed-batch operation.

In another embodiment, the fixed ratio of sucrose to maltose ranges between the ratios 1.5:1 to 7:1. In one embodiment, the fixed ratio is maintained at 2:1 or at 2.33:1 or at 2.75:1. In a further embodiment, the fixed ratio of sucrose to maltose is adjusted during the fermentation process by the addition of either more sucrose or more maltose.

In another embodiment, the dextransucrase-producing microorganism is *Leuconostoc mesenteroides* [in particular *Leuconostoc mesenteroides* ATCC 13146 or *Leuconostoc mesenteroides* NRRL B-742 or *Leuconostoc mesenteroides* subsp. *mesenteroides* (Tsenkovskii) van Tieghem (ATCC® 11449™), or NRRL B-1299], *Leuconostoc citreum, Leuconostoc gasicomitatum*, or *Leuconostoc kimchii*. In a further embodiment, the dextransucrase-producing microorganism is *Weisella confusa, Weissella cibaria, Lactococcus* spp, *Penicillium aculeatum, Pediococcus* spp (*pentosaceus*), *Streptococcus mutans, Streptococcus oralis, Streptococcus sanguinis*, or *Lactobacillis* spp (*reuteri*).

In another embodiment, the pH is controlled by adding an acid or a base to the culture medium. In a further embodiment, the base comprises an alkali earth metal hydroxide or carbonate. In one embodiment, the alkali earth metal is calcium. In another embodiment, the base comprises sodium hydroxide.

In one embodiment, the bacteria cells are removed by centrifugation, filtration or clarification. In another embodiment, the polishing removes insoluble impurities. In a further embodiment, the polishing comprises decolorization. In one embodiment, the decolorization utilizes activated charcoal or activated carbon. In a further embodiment, the decolorization comprises using a weak base anion resin. In yet another embodiment, the polishing comprises de-ashing. In one embodiment, the de-ashing comprises using a strong acid cation resin to remove metal ions. In another embodiment, the de-ashing comprises a two-step process using a strong acid followed by a weak base. In a further embodiment, the polishing comprises removing protein. In another embodiment, the removing protein comprises heating, then evaporating the aqueous culture medium followed by centrifugation or filtration. In one embodiment, the removing protein comprises using a weak base anion resin. In another embodiment, the polishing comprises removing organic acids. In one embodiment, the removing organic acids comprises utilizing a weak base anion resin. In another embodiment, the removing organic acids comprises liquid chromatography using a chromatographic grade gel-type strong acid cation exchange resin in calcium form (SAC-Ca++).

In another embodiment, the polishing comprises removing mannitol. In another embodiment, the removing the mannitol utilizes continuous or pulsed liquid chromatography. In a further embodiment the removing the mannitol utilizes evaporation followed by one or two stages of cooling to initiate crystallization and precipitation.

In another embodiment, the final composition of the oligosaccharides produced comprises isomaltooligosaccharides with one or more α-(1→4) at the reducing end and α-(1→6) linkages with a degree of polymerization between 3 and 9 or between 3 and 10. In a further embodiment, the isomaltooligosaccharides further comprise α-(1→4), α-(1→3) and/or α-(1→2) branching.

Another embodiment further comprises providing the oligosaccharides as a concentrated solution, optionally prepared under suitable conditions for human consumption. A separate embodiment further comprises providing the oligosaccharides as a powder, optionally prepared under conditions suitable for human consumption. In one embodiment, the powder is produced by drying, spray drying or by freeze drying.

In another aspect of the invention, a composition is produced by the method described above. Optionally, the composition is prepared under suitable conditions for human consumption.

Other objects of the invention may be apparent to one skilled in the art upon reading the following specification and claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 shows pH values needed for optimization of the yields of each oligomer. Maltose and panose should be minimized, and higher oligomers maximized.

DETAILED DESCRIPTION OF THE INVENTION

Figure 1:
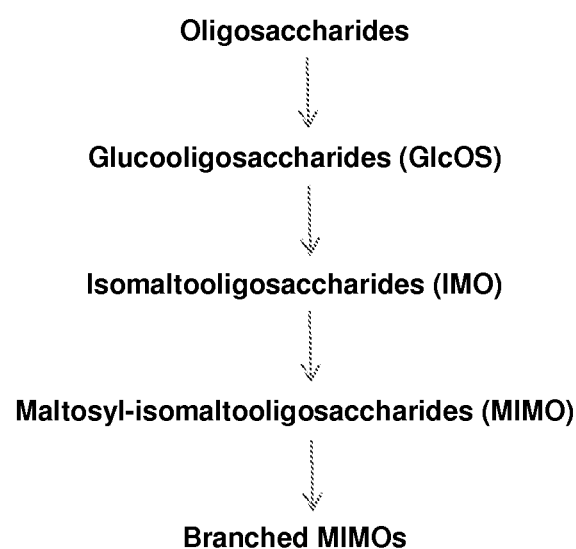
FIG. 1 shows the taxonomy of oligosaccharides.

This application is not limited to particular methodologies or the specific compositions described, as such may vary. It is also to be understood that the terminology used herein is for the purpose of describing particular embodiments only, and is not intended to be limiting, since the scope of the present application will be limited only by the appended claims and their equivalents. This application is related to U.S. application Ser. No. 14/833,094, filed Aug. 22, 2015, the contents of which are specifically incorporated by reference herein in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present application, the preferred methods and materials are now described. All publications mentioned herein are incorporated herein by reference to disclose and describe the methods and/or materials in connection with which the publications are cited.

Definitions

As utilized in accordance with the present disclosure, the following terms, unless otherwise indicated, shall be understood to have the following meanings:

"Brix", also known as degrees Brix (symbol ° Bx), refers to the sugar content of an aqueous solution. One degree Brix is 1 gram of sucrose in 100 grams of solution and represents the strength of the solution as percentage by weight (% w/w). Brix also accounts for dissolved salts, organic acids, and other solutes that increase the refractive index of the solution. As such, it is less useful as a quantitative measure of saccharide content in complex broth (fermentation mixtures), but is quite accurate with respect to the refined product. Thus, 1 degree brix=1 g refractive dry solids per 100 g of material. If the solution contains dissolved solids other than pure sucrose, then the ° Bx only approximates the dissolved solid content.

"Degree of polymerization", or "DP", refers to the number of sugar units in a given oligosaccharide.

"Oligosaccharides" refers to glycans of all kinds with DP>2 and <10.

"Glucooligosaccharide", or "GlcOS", refers to an oligosaccharide comprised of glucose in any structural arrangement. An example of a GlcOS is maltooligosaccharide [—O-α-(1,4)-], maltopentaose, which has the following chemical structure:

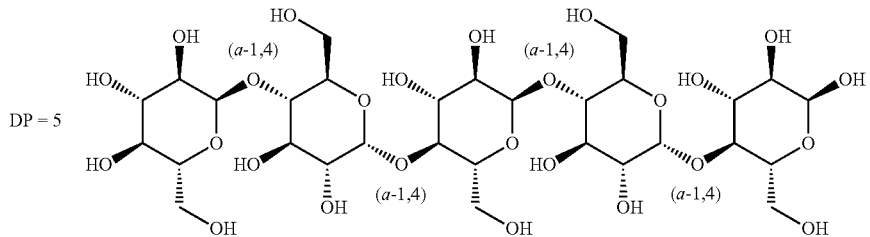 [SMILES: OC[C@H]1O[C@H](O[C@H]2[C@H](O)[C@@H](O)[C@@H](O[C@H]3[C@H](O)[C@@H](O)[C@@H](O[C@H]4[C@H](O)[C@@H](O)[C@@H](O[C@H]5[C@H](O)[C@@H](O)[C@@H](O)O[C@@H]5CO)O[C@@H]4CO)O[C@@H]3CO)O[C@@H]2CO)[C@H](O)[C@@H](O)[C@@H]1O]

"Isomaltooliaosaccharide", or "IMO", refers to glucosyl saccharides with a core structure based on an α-(1→6) linked backbone that may include α-(1→4), α-(1→3) (nigerooligosaccharides) and/or (kojioligosaccharides) linked branches. An example of an IMO is a GlcOS assembled with [—O-α-(1,6)-] linkages, isomaltopentaose, which has the following chemical structure:

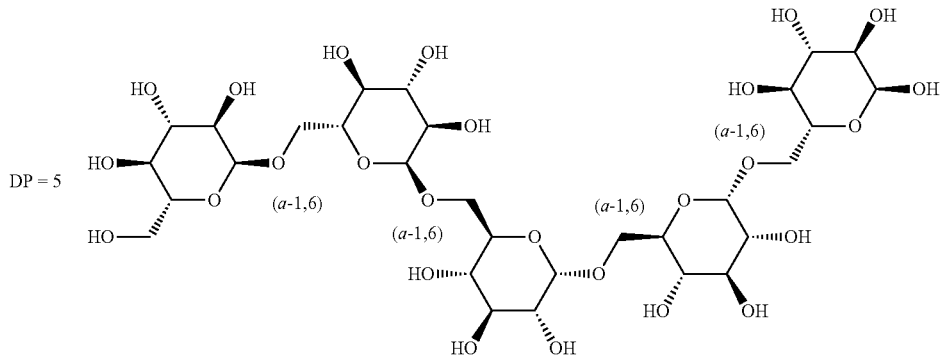 [SMILES: OC[C@H]1O[C@H](OC[C@H]2O[C@H](OC[C@H]3O[C@H](OC[C@H]4O[C@H](OC[C@H]5O[C@H](O)[C@H](O)[C@@H](O)[C@@H]5O)[C@H](O)[C@@H](O)[C@@H]4O)[C@H](O)[C@@H](O)[C@@H]3O)[C@H](O)[C@@H](O)[C@@H]2O)[C@H](O)[C@@H](O)[C@@H]1O]

"Maltosyl-isomaltooligosaccharides," or MIMOs, refers to an oligosaccharide, specifically glucan, of less than 10 degrees of polymerization comprised of α-(1→6) linkages terminated by an α-(1→4) linkage. The α-(1→4) terminal group is maltose, therefore maltosyl-isomaltooligosaccharide or MIMO is produced by an acceptor reaction by maltose or other maltooligosaccharide. An example of an MIMO with a single maltosyl linkage [—O-α-(1,4)-] linkage at the reducing end is maltosyl-isomaltotriose, which has the following chemical structure:

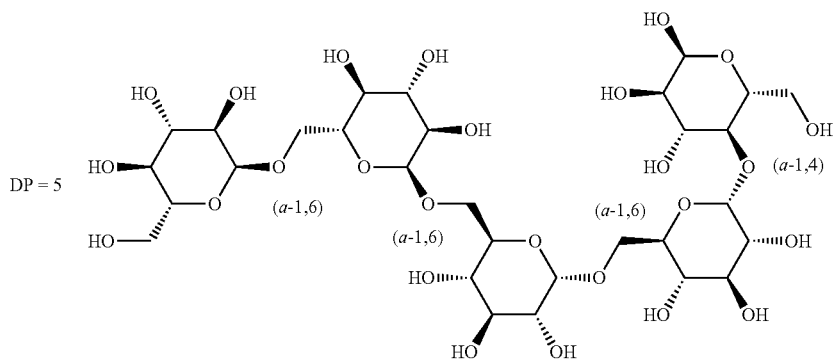 [SMILES: OC[C@H]1O[C@H](OC[C@H]2O[C@H](OC[C@H]3O[C@H](OC[C@H]4O[C@H](O[C@H]5[C@H](O)[C@@H](O)[C@@H](O)O[C@@H]5CO)[C@H](O)[C@@H](O)[C@@H]4O)[C@H](O)[C@@H](O)[C@@H]3O)[C@H](O)[C@@H](O)[C@@H]2O)[C@H](O)[C@@H](O)[C@@H]1O]

"Branched MIMO" refers to an oligosaccharide, specifically glucan, of less than 10 degrees of polymerization comprised of α-(1→6) linkages terminated by an α-(1→4) linkage and α-(1→2), α-(1→3) and/or α-(1→4) branches. Examples of a branched MIMO with glucose branching linkages at positions 1,2 and 1,3 and/or 1,4 have the following structures:

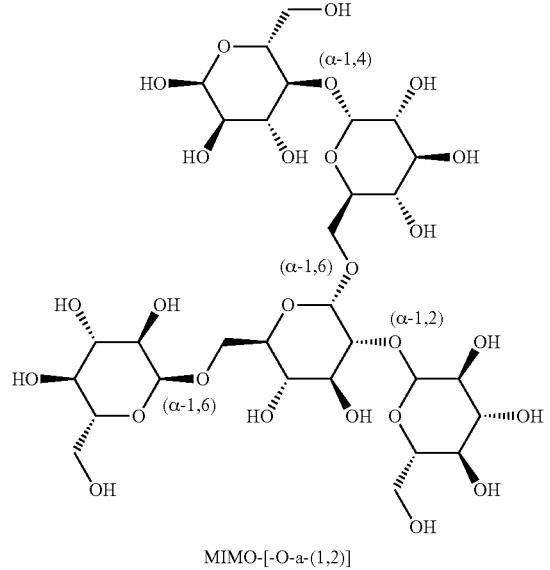

MIMO-[-O-a-(1,2)]

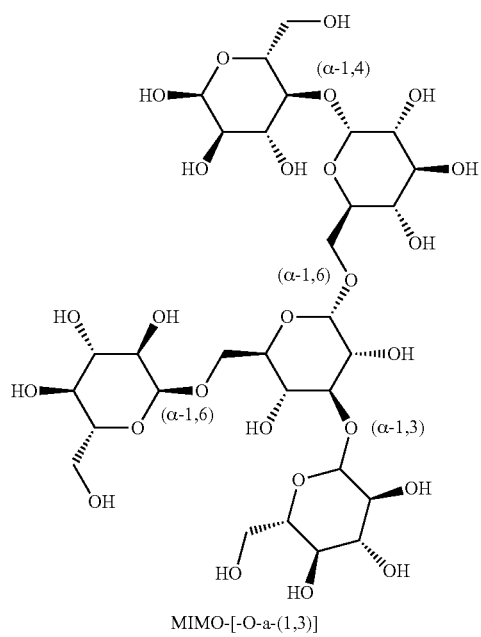

MIMO-[-O-a-(1,3)]

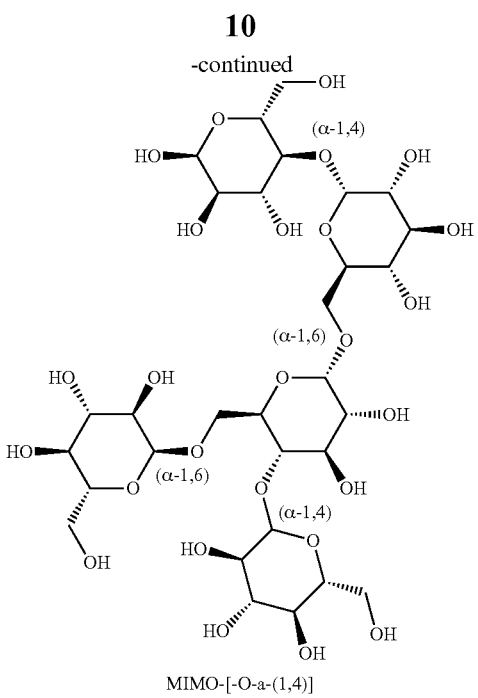

MIMO-[-O-a-(1,4)]

"Dietary supplement" refers to a food, food ingredient or food additive that produces a health benefit, including carbohydrates such as oligosaccharides.

"SAC" means a Strong Acid Cation exchange resin, typically one with sulfonic acid groups, i.e., a sulfuric acid equivalent.

"SBA" means a Strong Base Anion exchange resin, typically one with free amine groups, that can be made equivalent to hydroxyl groups.

"WAC" means a Weak Acid Cation exchange resin, typically one with free carboxylic acid groups (pKa ~4.2).

"WBA" means a Weak Base Anion exchange resin, typically one with tertiary amine groups which are not stronger than the corresponding free base (pKa ~9.8).

Reference will now be made in detail to certain preferred methods of treatment, compounds and methods of administering these compounds. The invention is not limited to those preferred compounds and methods but rather is defined by the claim(s) issuing herefrom.

Overview of the Invention

The glucooligosaccharides of the present disclosure are produced by the growth of L. mesenteroides (ATCC 13146) or any other dextransucrase-producing microorganism that produces the enzyme dextransucrase on sucrose in the presence of maltose or other receptor. The pH is adjusted prior to inoculation to 6.5-6.8 depending to the optimal pH to achieve maximum cell growth at the start of fermentation. It is also possible to adjust the starting pH to any level in the range of 4 to 8. The pH of the fermentation naturally drops from its starting pH as the organism grows in culture in the presence of an appropriate feedstock. The optimum pH for cell growth is 6.5 to 6.8. Optimum enzyme production and activity is in the range of 5.5 to 6.0. When pH 5.5 is reached, pH control is maintained by the addition of an alkaline material such as sodium hydroxide. The organism ATCC 13146 performs at an optimum pH of 5.5. In a preferred embodiment of the process of the invention, the pH of the fermentation broth is adjusted to pH 6.5 with 50% aqueous sodium hydroxide and is maintained around pH 5.5 during the desired length of the fermentation step.

Other dextransucrase-producing enzymes may prefer a different pH for optimum performance. Thus, in the process of the present invention, the initial pH is set to the preferred pH for the cell growth of the organism utilized. The pH is then allowed to drop naturally due to the production of organic acids during the process of the present invention to the pH that is the preferred for the specific dextransucrase-producing enzyme being utilized. If the pH is not controlled by external means, the pH of the fermentation broth will continue to drop until bacterial growth stops and the production of the desired maltosyl-isomaltooligosaccharides (IMOs) ceases.

The most desirable mixture of IMOs is produced during fermentation by bacterial enzyme(s) that carry out the fermentation process at an optimal pH of 5.5. Shifts in pH to values above or below 5.5 can alter both the yield and the mix of oligosaccharide sizes present in the product IMOs. Alternatively, this mix can also be changed by varying the starting sucrose to maltose ratio as well as varying the calcium content.

It is possible to increase the overall production of IMOs in a given fermentation by a continuous addition of a sucrose/maltose feed in the desired ratio of sucrose to maltose. This increase in product output and composition can be done independently of pH control if pH control is accomplished by the addition of an alkaline material such as sodium or potassium hydroxide, or can be done in conjunction with pH control if a sucrose containing material such as lime sucrate, supplemented with maltose, is used. Lime sucrate, also known as saccharate of lime, is a form of calcium hydroxide in which the calcium is complexed with sucrose.

The disclosed process also comprises an improvement on known commercial-scale methods for the fermentative production of GlcOS using *L. mesenteroides* (ATCC 13146) by reducing the cost of production. Costs associated with alkali can be reduced by a factor of ~2.4 by using $Ca(OH)_2$ rather than NaOH. Replacing two $Na^+$ ions with one $Ca^{2+}$ ion also negates the need for de-ashing the chromatographic ion exchange column, which eliminates two potentially expensive chromatographic steps. The use of lime sucrate solves the issue of solubility of calcium in water, and the sucrose-base is used as supplemental feedstock for the fermentation.

Disadvantages of Known Production Methods

Mixtures of isomaltooligosaccharides are generally produced by the action of immobilized enzymes on mono- or disaccharide feedstocks and can also be produced by transglycosylation of starch hydrolysates followed by chromatographic separation. In an early process, Chludzinski et al. produced branched isomaltooligosaccharides using dextransucrase (EC 2.4.1.5) expressed from bacterial cultures such as *Leuconostoc* spp. and *Streptococcus* ssp. (Chludzinski, A. M., et al., *J. Bacteriol.*, 1974, B:1-7). Roper and Koch later disclosed the production of isomaltooligosaccharide mixtures from starch hydrolysates (maltose and maltodextrins) through the action of the α-transglucosidase (EC 2.4.1.24) from *Aspergillus* sp. (*Starch*, 1988, 40:453-459).

More recently, use of the enzyme glucosyltransferase isolated from *Leuconostoc mesenteroides* has been reported. Remaud et al. disclosed the production of linear and short-branched oligosaccharides with α-(1→6) linkages and a maltose at the reducing end using a feedstock starting ratio of 7:1 sucrose:maltose from a reaction catalyzed by extracellular *Leuconostoc mesenteroides* ATCC 13146 glucosyltransferase (Remaud, M., et al., *J. Carbohydrate Chem.*, 1992, 11(3):359-378) producing branched dextrans with 1-3 linkages. The same group has reported the production of branched α-(1→2) isomaltooligosaccharide mixtures from sucrose with an acceptor reaction catalyzed by dextransucrase (Remaud-Simeon, M. et al., *Appl. Biochem. Biotechnol.*, 1994, 44:101-17). Paul et al. disclosed the synthesis and purification of branched isomaltooligosaccharide mixtures containing an α-(1→2) bond by the action of soluble and insoluble glucosyltransferase isolated from *Leuconostoc mesenteroides* B-1299 on sucrose and a glucosyl acceptor such as maltose (or a material rich in maltose, such as a starch hydrolysis product), isomaltose, methyl α-glucoside, isomaltotriose or glucose (or a material rich in glucose, such as a starch hydrolysis product) (Paul, F. et al., U.S. Pat. No. 5,141,858).

Chung and Day produced glucooligosaccharides (MIMO) generated in situ during fermentation via the action of dextransucrase generated in situ during live fermentation upon sucrose in the presence of a maltose acceptor (U.S. Pat. No. 7,291,607). The isomaltooligosaccharides produced were an extracellular product of the fermentation of sucrose by *Leuconostoc mesenteroides* ATCC 13146. Chung and Day demonstrated that these glucooligosaccharides (MIMO) are readily utilized by *bifidobacterium* sp. and *lactobacillus* sp., but not by *Escherichia coli* or *Salmonella* sp. in pure-culture studies (Chung, C. H. and Day, D. F., *J. Ind. Microbiol. Biotechnol.*, 2002, 29:196-9).

Immobilized enzymatic synthesis of isomaltooligosaccharides has been used to produce these compounds, but is a costly, complex process requiring enzyme isolation, immobilization and separation and likely requires more costly steps in purification of the end product. The method of the present invention is a step change improvement in how to make isomaltooligosaccharides in terms of efficiency of production and purity of the end product. The immobilized enzyme production approach also yields a different mix of molecules compared with the natural in situ fermentation process. Hence, the in situ approach is preferred for producing a natural product that may be more desirable as a dietary supplement than products produced by other methods.

Improved Method for the Production of Isomaltooligosaccharides

Conventional fermentation is a more practical approach for industrial manufacture of glucooligosaccharides, and in particular isomaltooligosaccharides, than the use of immobilized enzymes. Live cultures that produce dextransucrase in situ also metabolically convert the D-fructose to D-mannitol which can be economically separated. D-fructose is a difficult compound to separate from isomaltooligosaccharides and can be a detriment to use of this product in human nutrition, given the current information about the negative effects of high fructose syrups. (See: Ouyang, X., et al., *J. Hepatol.*, 2008, 48(6):993-9. doi: 10.1016/j.jhep.2008.02.011. Epub 2008 Mar. 10; Dhingra, R. et al., *Circulation*, 2007, 116:480-488; Swanson, J. E., eta., *Am. J. Clin. Nutr.*, 1992, 55(4):851-856; and Vartanian, L. R., et al., *Am. J. Public Health*, 2007, 97(4):667-75. Epub 2007 Feb. 28.)

By utilizing the method of the present invention, the size and composition of the product MIMOs may be closely controlled. The sucrose:maltose (S/M) ratio provides the primary control of product composition, in that it determines the general DP distribution. Close control of the pH of the fermentation mixture allows refinement of the product composition. Specifically, within the range of pH 6.5 to 5.5, the product composition bell curve shifts to higher DP as the pH decreases and vice versa. Introduction of specific amounts of $Ca^{++}$ also determines the degree of branching of the product MIMO by promoting one or more isoforms of dextransucrase (Chae, et al., *J. Microbiol. Biotechnol.*, 2009, 19(12): 1644-1649).

The composition of the MIMO produced is primarily determined by the bacteria utilized in the fermentation step. The action of bacteria genus species *Leuconostoc mesenteroides* ATCC 13146 on a sucrose/maltose mixture under the conditions of the present invention produces IMOs with α-(1→4) and α-(1→6) linkages with or without α-(1→4), α-(1→3) and α-(1→2) branching. The enzyme utilized by *Leuconostoc mesenteroides* to catalyze the linkage reaction, dextransucrase, has previously been isolated from various strains of the bacteria and used to produce similar IMOs. IMO synthesized by dextransucrase isolated from *Leuconostoc mesenteroides* ATCC 13146 had α-(1→6) backbones with α-(1→2), α-(1→3), and/or α-(1→4)-side chains when maltose was used as an acceptor (Remaud, M. et al., *J. Carbohyd. Chem.*, 1992, 11:359-378). It is reasonable to assume that MIMOs containing α-(1→2), α-(1→3), and α-(1→4) side chains will be effective prebiotics.

Any organism that produces dextransucrase is applicable for use in the process described herein. For example, as shown in FIG. 1, the GlcOS produced by the method of the present invention is a family of isomaltooligosaccharides that include, but are not limited to, branched isomaltooligosaccharides. The final mixture contains IMOs with DP2 to DP10, which are considered to be desirable prebiotics (Van Loo, J. et al., *Br. J. Nutr.*, 1999, 81:121-32). Dextransucrase from *Leuconostoc mesenteroides* strain ATCC 13146 reliably prefers to synthesize GlcOS with α-(1→6) linkages when maltose is used as the acceptor. The larger GlcOS oligomers (DP4 to DP8) may have continuous α-(1→6) linkages to maltose, that is, MIMOs. Many species of Leuconostocacea also produce branched MIMOs.

Any microorganism species capable of producing dextransucrase, including *Leuconostoc mesenteroides*, may be utilized in the process of the present invention. For example, *L. mesenteroides* ATCC 13146 may be used. This bacterium is known by other designations by those skilled in the art, including the designation *Leuconostoc citreum* ATCC 13146, the designation NRRL B-742, and the designation PWSA-*L. citreum* B742, the designation *Leuconostoc citreum* Farrow, and the designation *L. amelibiosum*. The bacterium *Leuconostoc mesenteroides* subsp. *mesenteroides* (Tsenkovskii) van Tieghem (ATCC® 11449™), NRRL B-1299, may also be employed. Other useful dextransucrase-producing microorganisms include, but not limited to, *Leuconostoc* spp (specifically *mesenteroides, citreum, gasicomitatum* and *kimchii*), *Weisella* spp (specifically *confusa*, such as NRRL # B 1064), *Lactococcus* spp., *Streptococcus* spp. (specifically *mutans*), *Lactobacillis* spp. (*reuteri*), *Pediococcus pentosaceus* spp., especially *Pediococcus pentosaceus* (ATCC #33316), and certain mutant *E. coli*. Useful microorganisms may also be isolated from natural sources including, but not limited to, sourdough wild starter (the bioorganism mixture used in the production of sourdough bread) and kimchi (a traditional fermented Korean dish made of vegetables and seasonings).

The feedstock ratio of sucrose to maltose (S:M) utilized in the process of the present invention is a determiner of the chemical composition of the product oligomer. In one embodiment, under batch conditions, the bacteria are grown in a nutrient mixture (culture medium) suitable to support growth of the bacteria and a fixed ratio of sucrose:maltose and fermentation is allowed to continue until all of the fructose generated during the reaction is converted to mannitol. The oligosaccharide production is complete when the sucrose is exhausted. Additional fermentation time may result in the reorganization of the MIMOs by chemical recombination that changes the DP distribution. In some cases, longer chains are formed, possibly from continued residual enzyme activity. Continuation until the fructose is converted to mannitol also simplifies purification of the final product. The further steps of the process, removing the spent bacteria cells, decolorizing the product and separating the mannitol and organic acids from the product oligosaccharides, are then carried out.

On a commercial scale, the method of the present invention is carried out in equipment known to those skilled in the art. Upon start-up of the fermentation process, the entire equipment system is flushed, cleaned and sterilized. A fermentation tank is charged with the requisite media components (typical vitamins, sulfates, phosphates, salts and other materials used for bacterial growth such as those media recommended by ATCC for use in growing the microorganism being cultured, including DIFCO® dehydrated culture media and ingredients) and sucrose and maltose in a defined ratio. Separately, the innoculum (in the preferred approach, ATCC 13146) is grown until achieving to OD-1 (Optical Density or absorbance at 660 nm via UV-VIS spectrophotometer) and added to the fermentation in a volume in the range of about 1% to about 10% of the amount contained in the fermentation. The fermentation takes place at a temperature around about 28° C. The fermentation is continued until no fructose is present, for a period of approximately 25 to 60 hours. The cells are separated from the broth by microfiltration, centrifugation or clarification and then discarded. The broth is decolorized through the use of granular activated charcoal at about 70 to about 80° C. Alternatively, powdered activated charcoal may be used and removed by filtration. The product is separated from the decolorized broth using pulsed or simulated moving bed chromatography at about 60 to about 65° C. The extract is then concentrated as desired and polished to remove the insoluble impurities, which can be performed through centrifugation or microfiltration. It can then be spray dried or freeze dried if the intent is to yield a powdered product.

In another embodiment, under fed-batch conditions, the process of the invention may run on a continuous, or semi-continuous basis. Additional feedstock may be introduced to keep the fermentation going and to manage the sucrose:maltose ratio. The pH may be controlled during the extended fermentation at the same time by the addition of sodium hydroxide, lime, lime sucrate or another suitable base as described below. As the initial feedstock is consumed, additional feedstock, either sucrose or maltose, may be added to the culture medium. Such feedstock additions may be used (a) to maintain the initial fixed sucrose:maltose ratio or (b) to change the sucrose:maltose ratio as the fermentation proceeds. In one embodiment, sucrose is added separately from the maltose to achieve a specific sucrose:maltose ratio. In another embodiment, maltose is added separately from the sucrose as a means to adjust the sucrose:maltose ratio. Such maltose-only addition may also prevent its degradation from continuous contact with the strong base prior to addition to the culture. Either approach may be used to produce the first-order MIMO end product with the desired chemical composition.

At any time during the extended fermentation, pH control may take place utilizing sodium hydroxide, lime, lime sucrate or other base. When lime sucrate is used, adjustments in feedstock addition, sucrose:maltose ratio, and pH control may take place simultaneously. Such fed-batch process may involve an input pump for each feedstock component and each pH control component, which allows for close control of the sucrose:maltose ratio and pH control. The product-containing broth is siphoned off and the other steps of the process carried out. In another embodiment, lime sucrate is added to the culture to control pH, in particular, to maintain a specific pH in the range of 5.5 to 6.8. It is also possible to add at the same time additional maltose so as to introduce a specific sucrose:maltose ratio with each dose of pH control. In another embodiment, the sucrose (or lime sucrate) and maltose may be mixed just prior to use, kept cool, and used immediately. In these ways, it is possible to control for sucrose:maltose ratio as well as pH at the same time whether using sodium hydroxide, lime, lime sucrate, or another base in order to achieve the desired MIMO chemical composition.

Under any of the embodiments disclosed herein, the sucrose:maltose ratio may range from 1.5:1 to 7:1. The sucrose:maltose ratio may range from 2:1 to 3.5:1. Preferably, the sucrose:maltose ratio ranges from 2:1 to 3.2:1. Additionally, the following sucrose:maltose ratios have utility: 2:1, 2.33:1; 3.17:1, and 3.2:1. All of these sucrose:maltose ratios can be utilized in the process of the invention to provide commercially desirable product MIMOs for mammalian or avian cosumption, preferably for human consumption. For example, a sucrose:maltose ratio of 2:1 produces a DP range of 4 to 7 using the process of the invention.

Varying the S:M ratio changes the degree of polymerization and the average molecular weight of the isomaltooligosaccharide distributions that are produced, shifting them to smaller average values as the amount of maltose increases relative to the sucrose. This appears to be a common effect for any dextransucrase producing organism, independent of strain (Day, D. F. and Yoo, S. K., "Natural Glucans: Production and Prospects," in R. A. Gross and C. Scholz (eds.), *Biopolymers from Polysaccharides and Agroproteins*, ACS Symposium Series, American Chemical Society, Washington D.C., 2001, 786:292-300). The degree of branching of MIMOs may be determined by the presence of appropriate amount of a divalent metal cation in the culture medium. While not wishing to be held by any particular theory, the divalent metal cation may influence the final IMO composition by forming a complex with the feedstock sugars, the active enzyme, or both. Appropriate divalent metal cations include, but are not limited to, calcium ($Ca^{++}$), magnesium ($Mg^{++}$), strontium ($Sr^{+++}$), zinc ($Zn^{++}$), manganese ($Mn^{++}$), and iron ($Fe^{++}$).

pH Control

Sodium hydroxide (NaOH) is routinely used as a pH control reagent in fermentation. For instance, the lactic acid bacteria, including *Leuconostoc* spp., need a significant amount of NaOH to maintain the optimum pH for their active growth due to the production organic acids during fermentation. Without pH control, the pH of *Leuconostoc mesenteroides* ATCC 13146 in fermentation rapidly drop to pH 3.5 within 10 hours (Dissertation, Yoo, Sun Kyun, "The Production of Glucooligosaccharides by *Leuconostoc mesenteroides* ATCC 13146 and *Lipomyces Starkeyi* ATCC 74054," 1997, Louisiana State University).

In the method of the present invention, the base utilized may be any hydroxide selected from the alkali or alkaline earth metals, including but not limited to, MgO, $MgOH_2$, CaO, $CaOH_2$, SrO, $Sr(OH)_2$, NaOH, LiOH, and KOH. In one embodiment, calcium hydroxide saccharates (sucrates) are preferred. The use of a calcium hydroxide sucrate permits addition of feedstock sucrose simultaneously with the base required to regulate pH at the desired level. For example, approximately a solution of 5% $CaOH_2$ in 25% sucrose is one desirable combination. $CaOH_2$ may be provided as slaked lime, lime or calcium oxide. In another embodiment, the base utilized may be an alkali earth metal carbonate.

The use of $CaOH_2$ obtained from lime has economic advantages in the present invention. As shown in Example 5 below, a two-liter fermentation required 16.2 g of NaOH to maintain a pH of 5.5. Using 2013 price information (see Example 5, Table 2, below), on a bulk basis the cost of NaOH would be $44.55 for a 10,000 L fermentation, while the cost of equivalent lime would be $18.15. On an industrial scale, lime ($0.14 per 10 kg product) can be a low cost alternative of NaOH, even if it is necessary to increase the amount of lime two-fold or more to maintain an appropriate pH. Lime sucrate method ($0.07 per 1 kg product) is more attractive because the solubility of lime is increased up to 5% in 22.5% sucrose solution (Dissertation, Madsen, L. R. "Iron Mediated Precipitation of Phenol: Protein Aggregates from Sugar Cane Juice", Louisiana State University, Baton Rouge, 2009) and feeding in maltose at the same time increased the observed yield of product over time.

The use of calcium as the basic counter-ion has process advantages. A cation (calcium, $Ca^{++}$ form) chromatographic exchange resin in this embodiment is used to separate the MIMO's from organic acids and mannitol. Due to the high concentration of sodium ions ($Na^+$) present in the fermentation broth, the sodium ions replace the calcium ions ($Ca^{++}$) in the resin used during separations. The presence of the calcium ions mitigates the need to regenerate the separation resins during processing. Thus, in the present method, the use of a calcium-ion-based alkali reduces the overall cost of the production of MIMOs.

Product Purification

Under the method of the present invention, the MIMOs are separated from the fermentation mixture after fermentation is complete as determined by the conversion of the fructose to mannitol. Alternatively, the fermentation is continued for a certain amount of time to allow the MIMOs produced to spontaneously rearrange themselves into longer chains, if desired in the end product. The amount of time needed for this rearrangement may be determined by conducting experiments as described herein in order to optimize the desired MIMO chain lengths.

The bacteria cells are then removed from the fermentation mixture, which is then subject to a de-ashing process in two steps (strong acid/weak base) and then decolorized. Mannitol is then removed through a crystallization process and the product MIMOs optionally then may be separated from the by-products via chromatography Alternatively, the MIMOs are separated from the fermentation mixture after fermentation is complete as determined by the conversion of the fructose to mannitol. In a further embodiment, the fermentation is continued for a certain amount of time to allow the MIMOs produced to spontaneously rearrange themselves into longer chains. The amount of time needed for the rearrangement may be determined by conducting experiments as described herein in order to optimize the desired MIMO chain lengths.

The bacterial cells are removed from the fermentation mixture, which is then decolorized, and subject to a de-ashing process in two steps: a strong acid followed by a weak base. Mannitol is then removed by using a single or a compound crystallization process. The product MIMOs may optionally be separated from the remaining by-products via chromatography.

Suitable methods for removing the bacterial cells include centrifugation, filtration or chemical clarification. In one embodiment, centrifugation is employed. Types of separation include continuous liquid or batch centrifugation, using a horizontal decanter, cream separator/disc centrifuge, and/or chemical clarification followed by decantation and/or filtration. Types of filtration include, but are not limited to, ultrafiltration, microfiltration or gel filtration.

Suitable methods for decolorization include, but are not limited to, the use of activated carbon in powder or granular form, with or without pH buffering (e.g. magnesite), and may be performed in either batch or continuous (e.g. column) mode. Activated charcoal may also be used. A suitable powered carbon is Carbochem CA-50 (Carbochem Inc., Wynnewood, Pa.) or an equivalent activated carbon. In batch mode, decolorizing carbon is added at about 60 to about 70° C., the bulk mixture is allowed to cool to a temperature of about 40° C., and after agitation, a filter aid is added. The bulk mixture is filtered to yield decolorized liquor.

In continuous mode, the bulk liquor is passed through a column charged with granulated activated carbon at about 65 to about 70° C. Once saturated, the carbon can be kilned or regenerated in-place via treatment with alkaline ethanol or equivalent (Bento). Examples of suitable filter aids include, but are not limited to, silicon dioxide, diatomaceous earth, diatomite, and kieselguhr. Suitable brand names include Celite® 545 (Sigma-Aldrich, St. Louis, Mo.) and Celatom® (Sigma-Aldrich). The grade of filter is selected according to the desired time for filtration to occur at an optimum rate, as finer grades will slow down the filtration significantly.

In a preferred embodiment, the bulk of the side-product mannitol can be removed by concentrating the mixture and cooling it until crystallization occurs. The crystals may then be separated via decantation, filtration or use of a basket centrifuge. Alternatively, fractional precipitation of products can be done using organic solvents such as ethanol.

Figure 5:
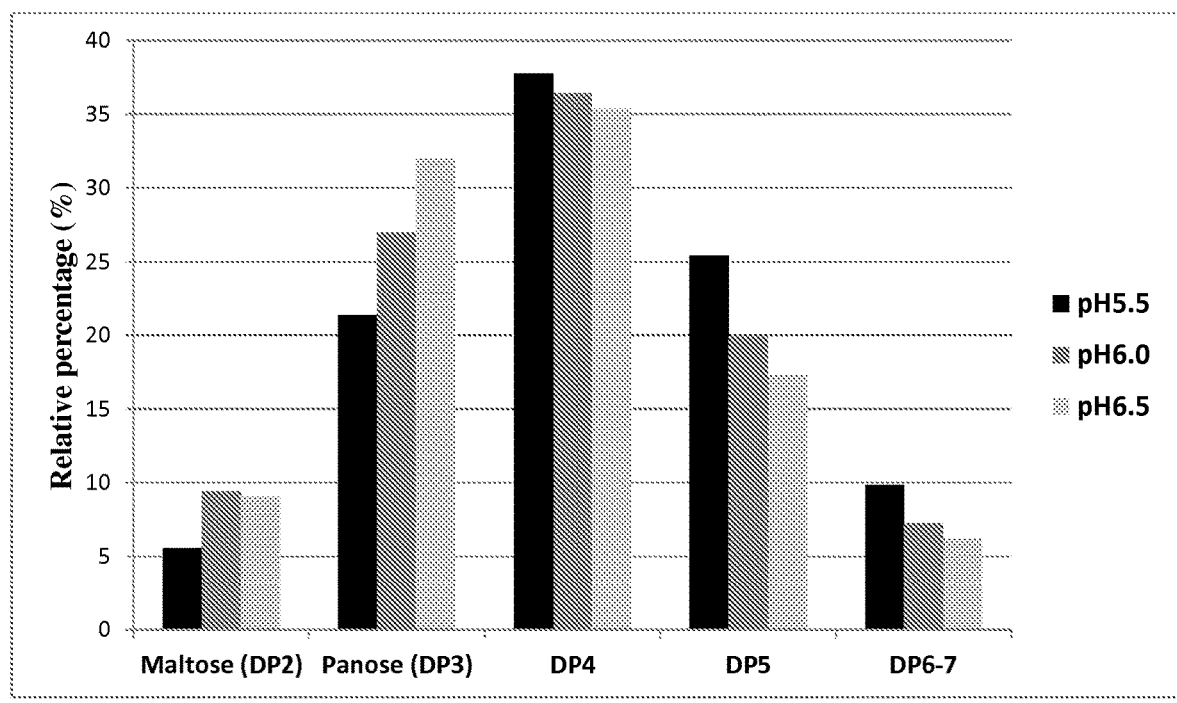
FIG. 5 shows a bar graph illustrating product patterns of maltosyl-isomaltooligosaccharides produced at different pHs as determined by HPLC. The bar graph gives the relative percentages. Samples were analyzed by high performance liquid chromatography (Agilent 1200 HPLC with a differential refractive index detector at 45° C., BioRad Aminex HPX-87K at 85° C. eluted with 0.01 M K2SO4 at 0.6 mL/min).

In another embodiment, the mannitol and the organic acids may be further removed by continuous or pulsed chromatography. (See FIG. 5.) For example, a chromatographic grade gel-type strong acid exchange (SAC) resin in calcium form (SAC-Ca) kept at 45-70° C. may be utilized. Two main fractions result from the chromatography: 1) MIMO plus acetic acid; and 2) mannitol plus lactic acid. It is possible that some lactic acid and some acetic acid may remain in the MIMO fraction after the completion of the chromatography without interfering with further processing.

If de-ashing is desirable, an anion exchange resin in partial free-base form may be used as described by Saska and Chen (U.S. Pat. No. 6,451,123). Alternatively, the oligosaccharide product-containing fraction may be further purified by removal of any heavy metal ions present utilizing an acid/base combination of ion exchange resins. Example combinations include, but are not limited to, SAC/SBA, SAC/WBA, WAC/SBA, and WAC/WBA in series, or used as mixed-resin beds.

In a preferred embodiment, decolorization occurs prior to de-ashing so as to protect the de-ashing resins from contamination of the color bodies. Also, the use of WBA vs SBA offers three key improvements: (1) the WBA removes all of the organic acids that would otherwise only be partially removed by liquid chromatography, (2) removes any residual proteins in the fermentation broth and (3) removes any residual color that was not removed via the activated carbon step. Removal of the residual color is important because the resin can be irreversibly fouled without this step. By using this specific de-ashing set, additional downstream options for final product polishing such as mannitol crystallization become available in addition to liquid chromatography or both in combination.

In a further embodiment, the MIMO-containing liquor is concentrated by evaporation to give a solution with a brix range between about 20 and about 70 (gram refractive dry solids/100 g). Other possible brix ranges are between about 30 to about 65, between about 50 to about 60, between about 55 to about 65, and between about 55 to about 59. Other brix ranges may be preferred for specific end-product uses.

In another embodiment, the mannitol may be further removed by continuous or pulsed chromatography. See FIG. 5. For example, a chromatographic grade gel-type strong acid exchange (SAC) resin in calcium form (SAC-Ca) kept at 45-70° C. may be utilized. Two main fractions result from the chromatography, MIMO and mannitol, with some residual mannitol remaining in the MIMO fraction.

In a further embodiment, the MIMO-containing liquor is concentrated by evaporation to give a solution with a brix range between 20 and 70 (gram refractive dry solids/100 g). Other possible brix ranges are between about 30 to about 65, between about 50 to about 60, between about 55 to about 65, and between about 55 to about 59. Other brix ranges may be preferred for specific end-product uses.

In yet another embodiment, the MIMO is made into a powder by spray drying or by freeze drying or other forms of vacuum evaporation. Alternatively, the purified liquor may be precipitated with ethanol or a similar solvent to yield a solid product that is easily dried.

The following examples are offered by way of illustration and not by way of limitation.

EXAMPLES

Example 1

Preparation of Bacterial Strain and Culture Medium

*L. citreum* was purchased from the American Type Culture Collection (ATCC 13146, Manassas, Va.). After re-isolation, the strain was stored in a −74° C. freezer in 20% glycerol. This two-liter culture was grown at 28° C. in a medium composed of sucrose (100 g/L), maltose (50 g/L), yeast extract (5 g/L), $MgSO_4.7H_2O$ (0.2 g/L), $FeSO_4.7H_2O$ (0.01 g/L), NaCl (0.01 g/L), $MnSO_4.7H_2O$ (0.01 g/L), $CaCl_2$ (0.05 g/L), $KH_2PO_4$ (3 g/L at pH 6.5). For two-liter fermentations, yeast extract (10 g), $MgSO_4.7H_2O$ (400 mg), $FeSO_4.7H_2O$ (20 mg), NaCl (20 mg), $MnSO_4.7H_2O$ (20 mg), $CaCl_2$ (100 mg), and $KH_2PO_4$ (6 g) were dissolved in distilled water (1250 mL) and adjusted to pH 6.5 using 6 M NaOH prior to innoculation. The mixture was autoclaved for 15 min at 120° C. Solutions of maltose (100 g/250 mL) and sucrose (200 g/500 mL) were sterilized prior to transfer to the fermentor.

Example 2 pH Control-Materials and Preparations

The pH control capacity of lime was compared with sodium hydroxide (NaOH). Sodium hydroxide pellets were purchased from Fisher Scientific (Hanover Park, Ill.) and hydrated lime powder was purchased from Batesville Marble Hydrated Lime (Arkansas Lime Company, Batesville, Ark.). NaOH (5% w/v, 1.25M, 1.25M eq. [$OH^-$]) and lime (5% w/v, 0.68M, 1.35M eq. [$OH^-$]) solutions were prepared by dissolving 50 g of each in 1 L distilled water. To prepare a 5% lime sucrate solution, lime powder (50 g in 1 L bottle) and sucrose (250 g in 805 mL distilled water) were autoclaved separately. After autoclaving, sucrose solution was transferred into the 50 g of lime to give a final solution concentration of 5% lime in 25% sucrose, and given the identification "5% lime sucrate". A solution of maltose (1 L of 12.5%) was also prepared separately.

Example 3

Fermentation and pH Control

Batch fermentations were conducted using 2 L BioFlo II fermentors (New Brunswick Scientific, New Brunswick, N.J.). The fermentors were inoculated from late log-phase flask seed cultures at 1.0% (20 mL) of working volume. Fermentations were conducted at 28° C. with stirring at 200 rpm.

The pH of the cultures decreased from a starting pH of 6.5 as the cells produced organic acid and continued to drop until automatic control began, when pH reached 5.5 (optimal for the dextransucrase used). This took about 5.5 hrs. The pH was maintained at 5.5 until completion of the fermentation (30 hrs) using 5% NaOH (w/v), 5% lime (w/v), or 5% lime sucrate (together with 12.5% w/v maltose solution). A feed of 5% lime sucrate and 12.5% maltose were used to adjust pH and maintain a sucrose to maltose ratio at 2:1. For the lime sucrate method, the lime sucrate and maltose were fed separately with same flow rate for the initial 18 hours to control the pH and then replaced with a lime solution for 12 hours until the end (30 hours) to avoid the residual fructose in the final fermentation broths.

Example 4

Purification of MIMOs, Mannitol, and Organic Acids

After harvesting, cells were removed by centrifugation at 10,400 g for 20 min. Activated charcoal (5 g/L, Sigma, St. Louis, Mo.; 100400 mesh) and Celite 545 (1 g/L, Fisher Scientific, Hanover Park, Ill.) was added to cell-free culture broth and mixed at 50° C. for 20 min. The broth was filtered through No. 3 filter paper (Whatman, Maidstone, England) to remove the carbon. The filtered broth was concentrated using a Yamato rotary evaporator RE71 (Yamato, Santa Clara, Calif.) at 65° C. to 85° C. to 57 g/100 g (° brix).

Cation-exchange chromatography (6.0×70 cm column) with pre-swelled Dowex Monosphere 99 320 resin (sulfonated styrene-DVB, 300-330 μm, gel, 1.5 eq/L [H+], $Ca^{++}$ form; Dow, Midland, Mich.) was used to separate the MIMOs. (See FIG. 5.) Elution was monitored in real-time by periodically measuring the refractometer brix (Atago Pallet). During elution, the void volume was discarded and then fractions were collected and analyzed for both carbohydrates and acids by HPLC.

Figure 3:
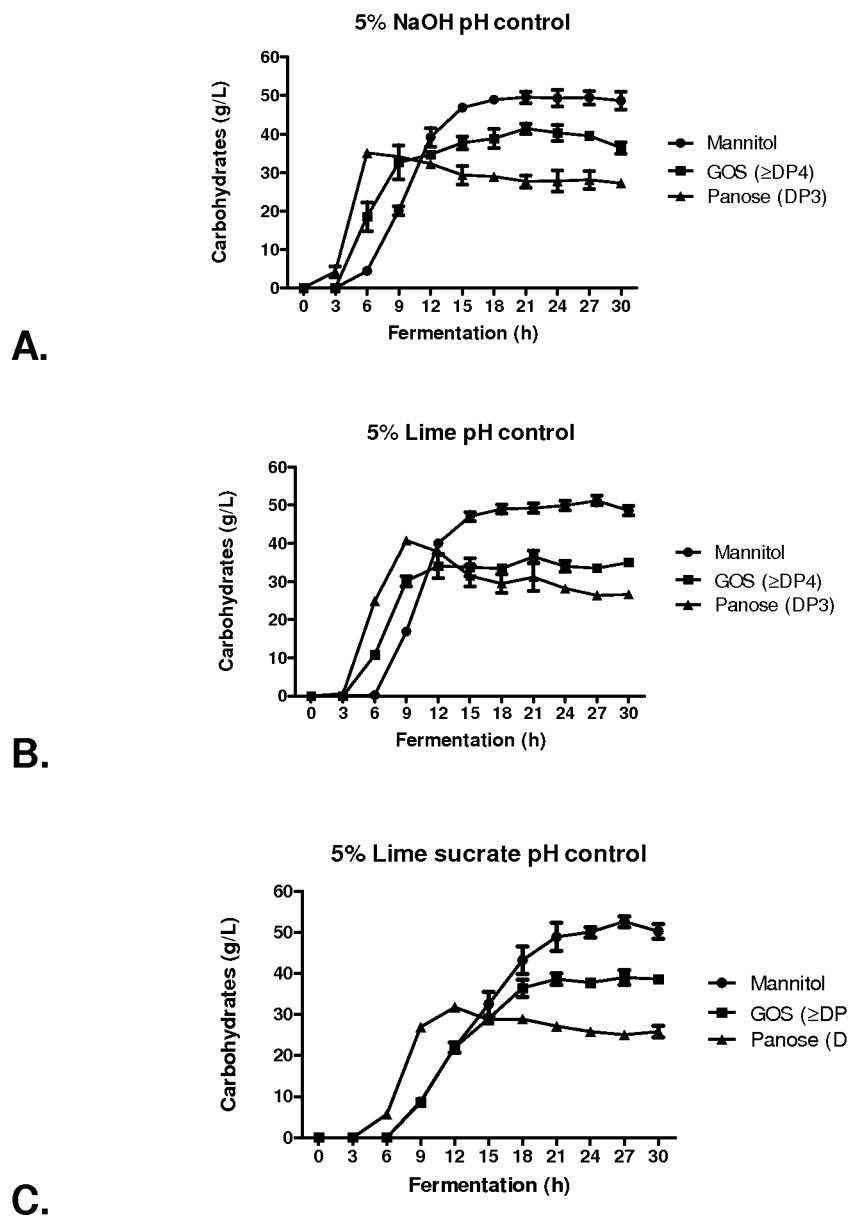
FIG. 3 illustrates the production patterns of glucooligosaccharides and mannitol by *L. mesenteroides* ATCC 13146 from sucrose and maltose as a function of time. Fermentation of *L. mesenteroides* ATCC 13146 with (A) 5% NaOH pH control; (B) 5% Lime pH control; and (C) 5% Lime sucrate pH control. Fermentation samples (carbohydrates) harvested according to the times shown were analyzed by high performance liquid chromatography (Agilent 1200 HPLC with a differential refractive index detector at 45° C., BioRad Aminex® HPX-87K at 85° C. eluted with 0.01 M $K_2SO_4$ at 0.8 mL/min).

Based on the results of HPLC analysis (or brix), MIMO fractions containing either MIMO:acetic acid or mannitol:lactic acid were combined. After concentration to 30° brix, the mannitol was separated from the lactic acid via ethanolic precipitation (70% ethanol). The precipitated solid fraction (mannitol) was washed again with 100% ethanol and air-dried at 55° C. The MIMO fraction and lactic acid fractions were freeze-dried. The acetic acid is volatile and the bulk of it was removed during lyophilization. (See FIG. 3.)

Example 5

Purification of MIMOs, Mannitol, and Organic Acids

After harvesting, cells were removed by centrifugation at 9-14 k*g for 20-30 min. Activated charcoal (0.5-3.0% w/w, Carbochem DC-50, or equivalent) was added to cell-free culture broth and mixed at 40-70° C. for 20-60 min. The broth was filtered through No. 3 filter paper (Whatman, Maidstone, England) topped with diatomite filter aid (fast-flow, Celite 545 or equivalent, 1.0-6.0% w/w) to remove the carbon. The filtered broth was concentrated using a Buchi R-220 rotary evaporator at 65° C. to 85° C. to 57 g/100 g (° brix).

Example 6

Comparing MIMO Production with Lime, Lime-Sucrate or Sodium Hydroxide

Figure 2A:
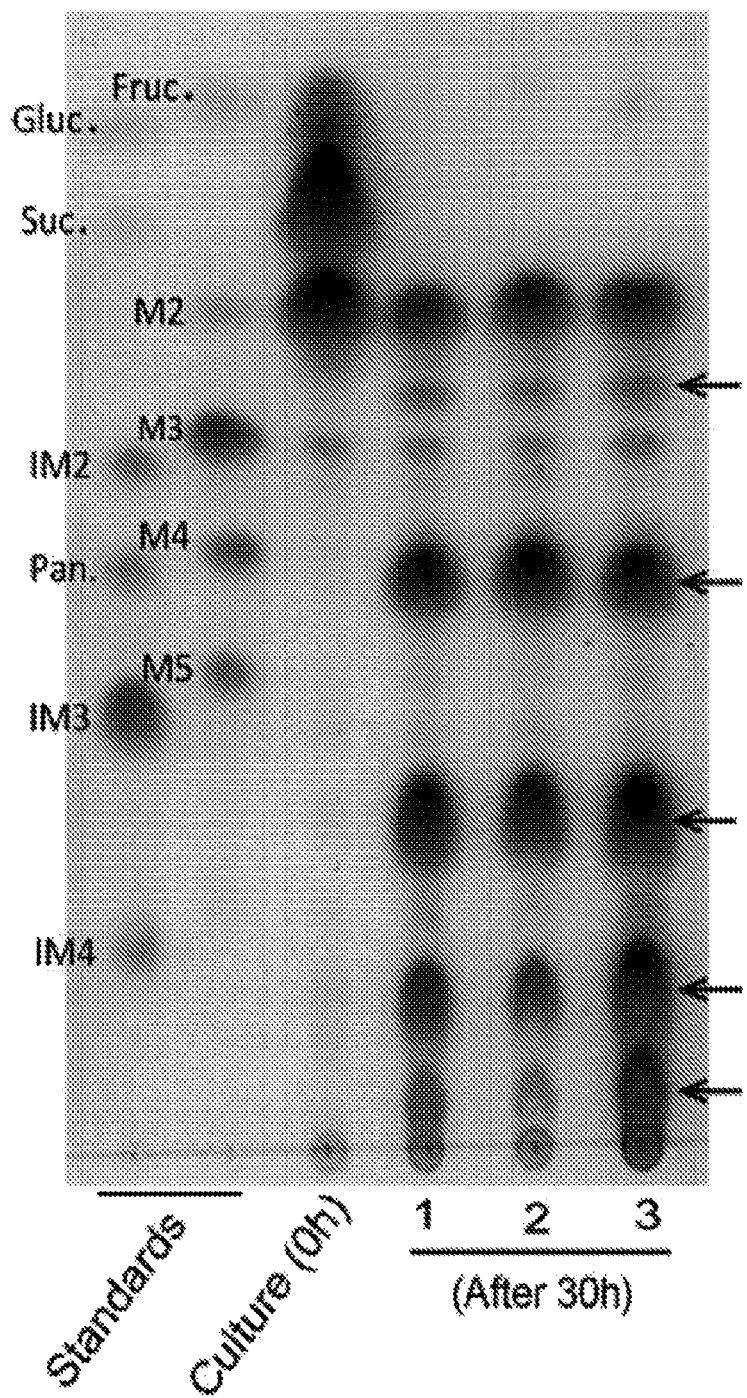
FIG. 2A depicts a thin-layer chromatograph (TLC) of glucooligosaccharides of *L. mesenteroides* ATCC 13146 fermentations with three pH control methods wherein Lane 1 shows a 5% NaOH fermentation batch; Lane 2, a 5% lime fermentation batch; and Lane 3, a 5% lime sucrate fermentation batch. The following abbreviations are shown in the figure: Gluc., glucose; Fruc., fructose; Suc., sucrose; IM2, isomaltose; IM3, isomaltotriose; IM4, isomaltotetraose; M2, maltose; M3, maltotriose; M4, maltotetraose; M5, maltopentaose.
Figure 2B:
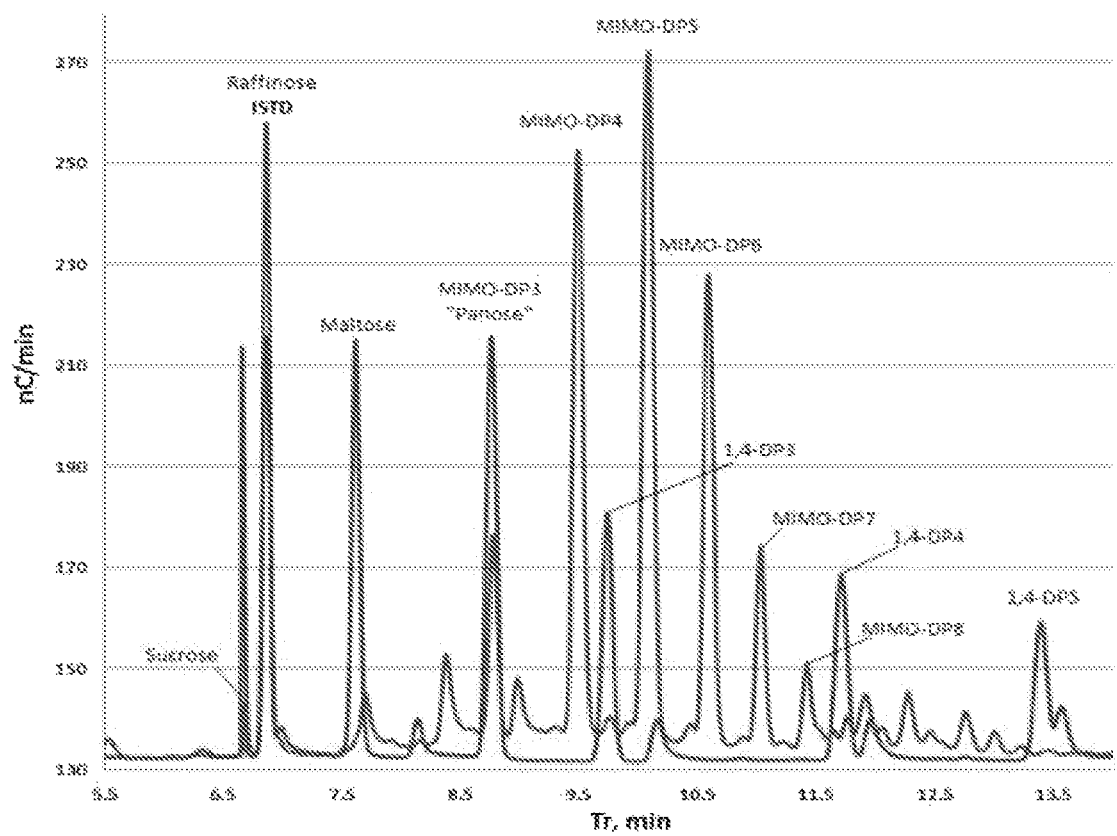
FIG. 2B depicts a typical HPAEC chromatogram, for comparison. The blue line represents a typical product, and the red line represents a standard (1,4-DPx=maltosyl oligosaccharide or DPx).

Using lime rather than NaOH for pH control, GlcOS was produced from *Leuconostoc mesenteroides* ATCC 13146 according to the method of Chung and Day (2004, *Poult. Sci.*, 83:1302-6). Progress was monitored via TLC. The GlcOS products (indicated by arrows in FIG. 2) were primarily DP3 (Degree of Polymerization, panose) through DP6 polysaccharides with $R_f$ values corresponding to neither maltooligosaccharides (M2-M5) nor isomaltooligosaccharides (IM2-IM4).

Once the fermentations were complete, as assessed by TLC, the yields of GlcOS (DP≥3), mannitol, and maltose produced using pH control with 5% NaOH or 5% lime or 5% lime sucrate, with 12.5% maltose were compared in terms of total GlcOS as determined by HPLC. Table 1 shows the GlcOS production by weight percent of the carbohydrate feed.

TABLE 1

| Product | NaOH | Lime | Lime sucrate |
| --- | --- | --- | --- |
| GlcOS (DG ≥ 3) | 42.40 ± 1.50 | 41.40 ± 0.51 | 40.00 ± 1.35 |
| Mannitol | 32.45 ± 1.49 | 32.42 ± 0.82 | 31.15 ± 1.26 |
| Maltose | 12.85 ± 1.61 | 12.45 ± 0.31 | 12.96 ± 0.80 |

Figure 4:
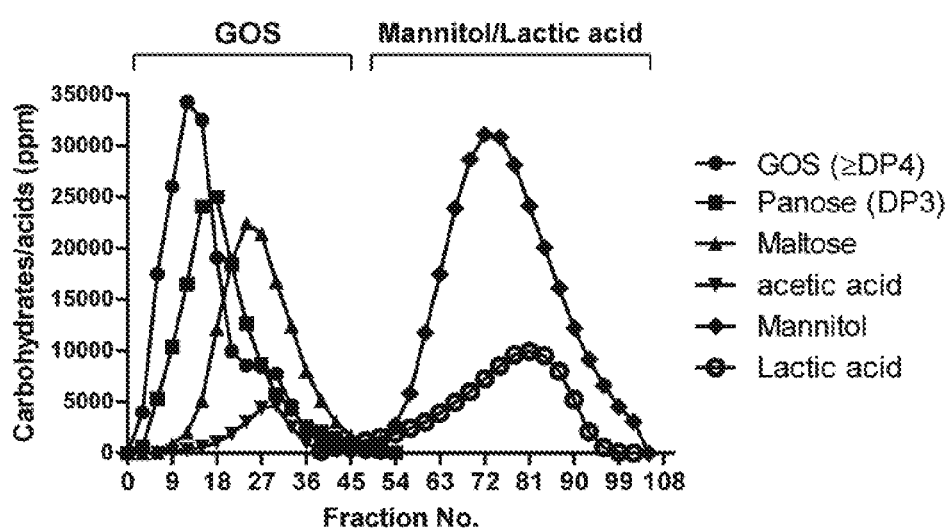
FIG. 4 shows an HPLC analysis where cation resin chromatography (60 mL loading with 57 Brix sample) was carried out with 10 mL/min flow rate at 50° C., where fractions (each 15 mL) were collected. For carbohydrates (GIcOS (marked as GOS), panose, maltose, and mannitol), Agilent 1200 HPLC was used with a differential refractive index detector at 45° C., BioRad Aminex HPX-87K at 85° C. eluted with 0.01 M $K_2SO_4$ at 0.8 mL/min. For organic acids (acetic acid and lactic acid), Agilent 1100 HPLC was used with an Aminex HPX-87H column at 65° C. eluted with 1.0 mL/min of 0.005 N $H_2SO4$ with detection via absorbance at 210 nm.

Using lime, the yields (% of GlcOS (DP≥3) per total carbohydrate amount input) were similar (42.4±0.51%) with the NaOH (41.1±1.50%) control (Table 1). In all fermentations, the production of GOS (DP≥3) and mannitol were complete approximately 15 h and 21 h post-inoculation depending on the type of pH control used (FIG. 4). With 5% lime sucrate, the final GlcOS production (387.7 g) was greater than with NaOH (Table 2) and the 40.0±1.35% yield (GlcOS (DP≥3) per total carbohydrate amount input) was slightly lower than the 42.4±1.50% observed using 5% NaOH (Table 1).

TABLE 2

| Fermentations | NaOH[a] (g per 2 L) | Lime[a] (g per 2 L) | Total carbohydrates (g per 2 L) (sucrose/maltose) | Product[b] (g per 2 L) | Cost of NaOH or Lime[c] (10 kL ferment) | pH control cost per 10 kg of GlcOS |
|---|---|---|---|---|---|---|
| NaOH | 16.2 g | | 300 g | 263.5 g | $44.55 | $0.33 |
| Lime | | 26.3 g | 300 g | 257.9 g | $18.15 | $0.14 |
| Lime sucrate | | 21.5 g | 461.25 g | 387.7 g | $14.84 | $0.07 |

[a]Amounts of NaOH and lime used for 2 L fermentations.
[b]The final products are GlcOS (DP ≥ 3), mannitol, and maltose.
[c]Price of NaOH ($550 per metric ton) per global chemical market intelligence service ICIS pricing on May, 2013 (at world wide web URL icis.com/Articles/2013/05/02/9664807/three-us-producers-announce-price- initiatives-for-caustic.html). Price of hydrated lime ($138 per metric ton) in the United States (personal communication, M. Michael Miller, Lime Specialist, U.S. Geological Survey, Dec. 3, 2013).

A two-liter fermentation required 16.2 g of NaOH, 26.3 g of lime, and 21.5 g of lime sucrate to maintain the optimum pH. The costs of either NaOH or lime relative to the respective product yield were calculated and are given in Table 2.

Example 7 pH Control of Maltosyl-Isomaltooliqcosaccharides Product Patterns

Maltosyl-isomaltooligosaccharides are produced by fermentation of sucrose in the presence of maltose by the organism L. mesenteroides ATCC 13146. Generally, the pH of the fermentation medium drops from its preferred starting pH of 6.5-6.8 to 5.5-4.5 as the organism grows. In this example, maltosyl-isomaltooligosaccharides were produced from fermentation at three different pHs (pH 6.5, pH 6.0, and pH 5.5).

Batch fermentations were conducted in 10 L BioFlo fermentors (New Brunswick Scientific, New Brunswick, N.J.). The fermentors were inoculated from late log-phase flask seed cultures at 1.0% (100 mL) of working volume. Fermentations were conducted at 28° C. with stirring at 200 rpm. To maintain the fermentation medium was initially set at a pH of 6.5, and allowed to drop during fermentation to pH 5.5, and thereafter maintained at pH 5.5 using 10 N NaOH fed by automatic pH control. If different process pH values were required, the same process was used, except that the automatic control was set to start at the desired fermentation pH.

Figure 6:
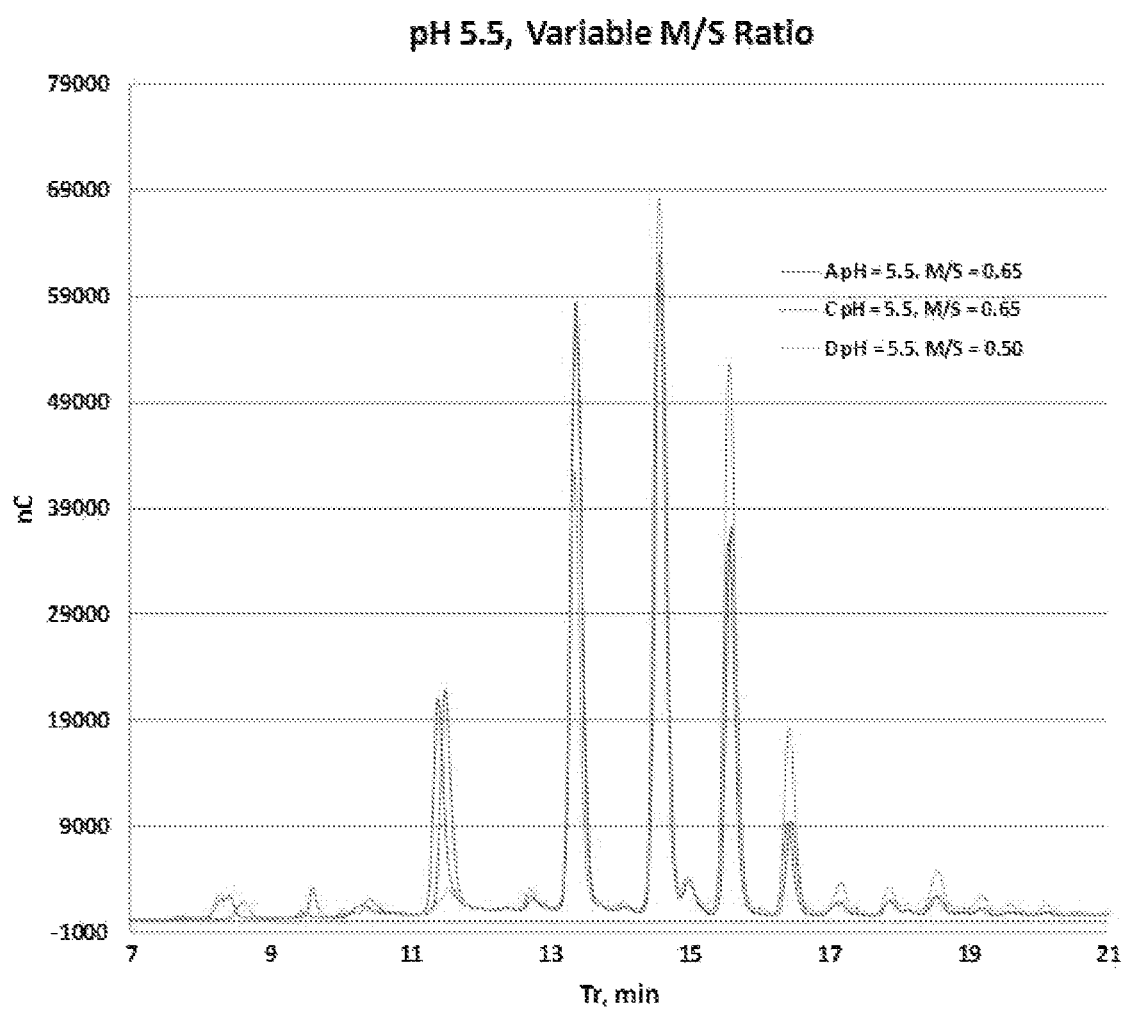
FIG. 6 shows the effect the sucrose:maltose (S/M) ratio has on the molecular weight distribution at a fixed pH of 5.5. As S/M increases, so does the molecular weight distribution.

High performance liquid chromatography (Agilent 1200 HPLC with a differential refractive index detector at 45° C., BioRad Aminex HPX-87K at 85° C. eluted with 100% water at 0.6 mL/min) was used for quantitative analysis of carbohydrates. A three-point curve made of maltose, panose, mannitol, glucose, and fructose was used to standardize the instrument. The final patterns of maltosyl-isomaltooligosaccharides produced differed according to the pH maintained during the fermentation process. As shown in FIG. 6, a bar graph of the data from Table 3, a lower pH produced longer oligomers (DP 4-7) of maltosyl-isomaltooligosaccharides, while higher pH yielded the shorter oligomers maltose or panose (DP 2-3).

TABLE 3

| pH | Maltose (DP2) | Panose (DP3) | DP4 | DP5 | DP 6-7 |
|---|---|---|---|---|---|
| 5.5 | 5.58 | 21.37 | 37.75 | 25.45 | 9.86 |
| 6.0 | 9.41 | 27.02 | 36.44 | 19.88 | 7.25 |
| 6.5 | 9.07 | 31.98 | 35.39 | 17.33 | 6.24 |

Figure 7:
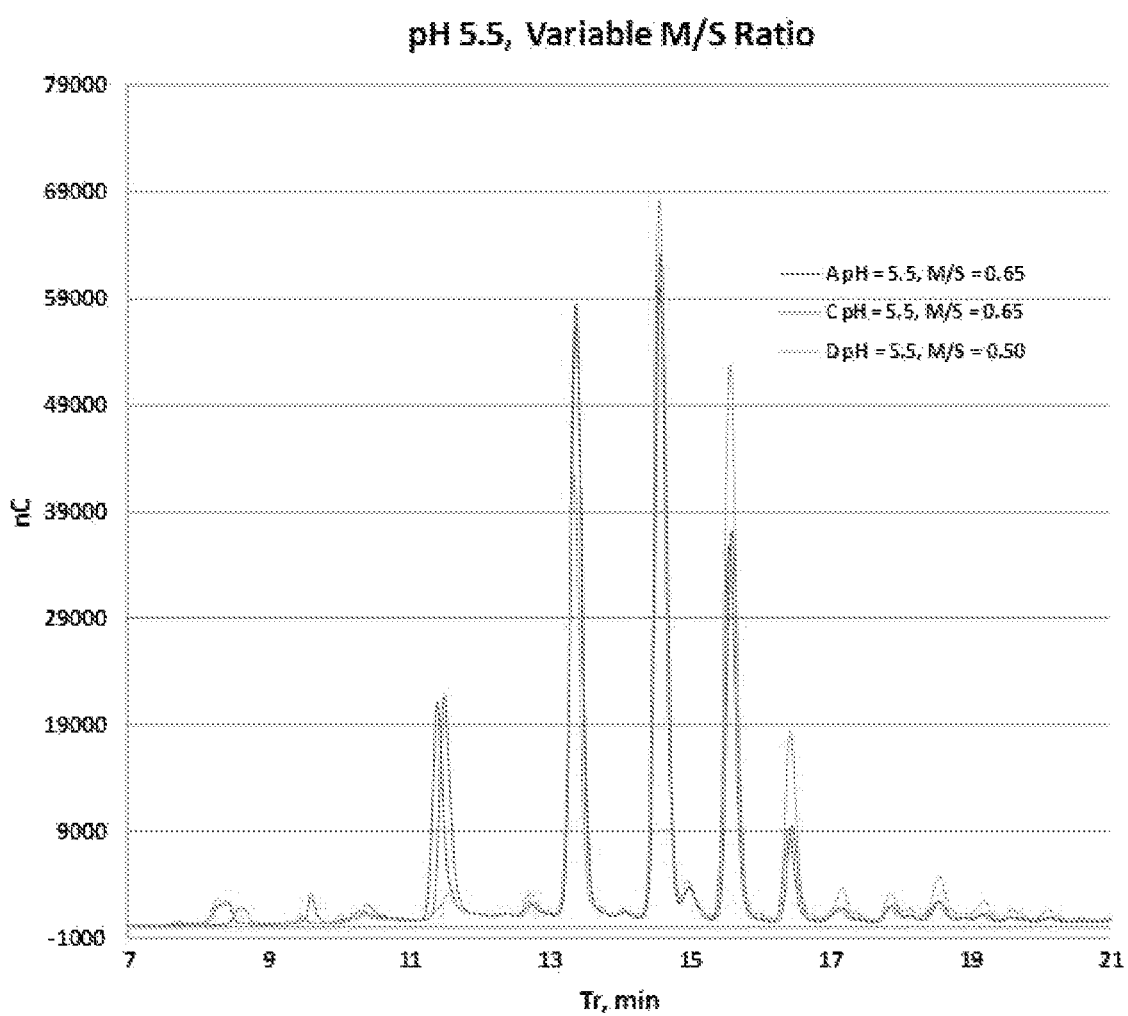
FIG. 7 shows the effect that pH has on the molecular weight distribution at fixed sucrose:maltose (S/M) ratio. As pH decreases toward 5.5, the molecular weight distribution increases.

FIG. 7 shows the effect the sucrose:maltose (S/M) ratio has on the molecular weight distribution at a fixed pH of 5.5. As S/M increases, so does the molecular weight distribution. Additional experiments were conducted at three different fermentation pHs. Profiles of each carbohydrate component during these fermentations at three different pHs were compiled and included monitoring of cell growth density, sucrose, maltose, mannitol, monomers (glucose, fructose), and maltosyl-isomaltooligosaccharides polymers (DP 3-7).

Example 8

Effect of Sucrose:Maltose Ratio on Product Composition

Oligosaccharides were produced according to the method previously described. However, the sucrose to maltose ratio (S/M) was varied in order to determine the optimum ratios for the production of maltosyl-isomaltooligosaccharides in various ranges of degree of polymerization (DP). Fermentation samples were analyzed via HPAEC-PAD (high pressure ion exchange chromatography using a Thermo Dionex ICS-5000 with a Carbopac PA-100 column and a pulsed amperometric detector).

FIG. 8 demonstrates the effect of pH when the S/M is fixed at 2:1. It is clear that the closer the pH approaches the enzyme's optimum, the greater the proportion of higher molecular weight oligosaccharides. It is also evident that maltose conversion becomes more efficient at pH<6.8 and that panose is glycated at a greater rate.

Example 9

Use of Different Dextransucrase-Producing Microorganisms

Leuconostoc spp. ATCC 13146 and Kimchi were evaluated through the same process as that set forth for the present invention. The Kimchi juice was sequenced by PCR to review 16SrRNA to determine the bacterial species in the Kimchi juice and confirmed the presence of Leuconostoc spp. (comprising 72.5% of the bacteria present in the juice) capable of making dextransucrase. See Table 4 below. In the case of NRRL 1299, the species was cultured from revived freeze dried isolates provided by ATCC. With Kimchi, the active fermenting juice was used as the innoculum. In each case, after the sugar and nutrient media were prepared, it was sterilized in place in the fermenter and then inoculated. The inoculum was prepared by growing the bacteria to OD-1 (Optical density or absorbance at 660 nm via UV-VIS spectrophotometer). The pH in the fermenter was adjusted with sodium hydroxide to 6.5 at initial fermentation. The fermentation of the media was carried out for 25 to 65 hours until complete as described in the present invention. During fermentation the pH was allowed to drop to 5.5 and then maintained at 5.5 by controlled addition of sodium hydroxide. The cells were then removed using centrifugation and the resulting clear liquor was decolorized with powdered carbon. The resulting broth was then purified by chromatography. The resulting purified liquor was concentrated to 55 to 65 brix and the resulting syrup was centrifuged to remove proteins and other solids.

TABLE 4

| Sample ID | Species | Kimchi Juice |
|---|---|---|
| NR 102781 | Leuconostoc carnosum JB16 | 6.8% |
| NR 074997 | Leuconostoc gasicomitatum LMG | 42.1% |
| NR 102984 | Leuconostoc gelidum JB7 | 12.2% |
| NR 025204 | Leuconostoc inhae strain IH003 | 2.6% |

Figure 9:
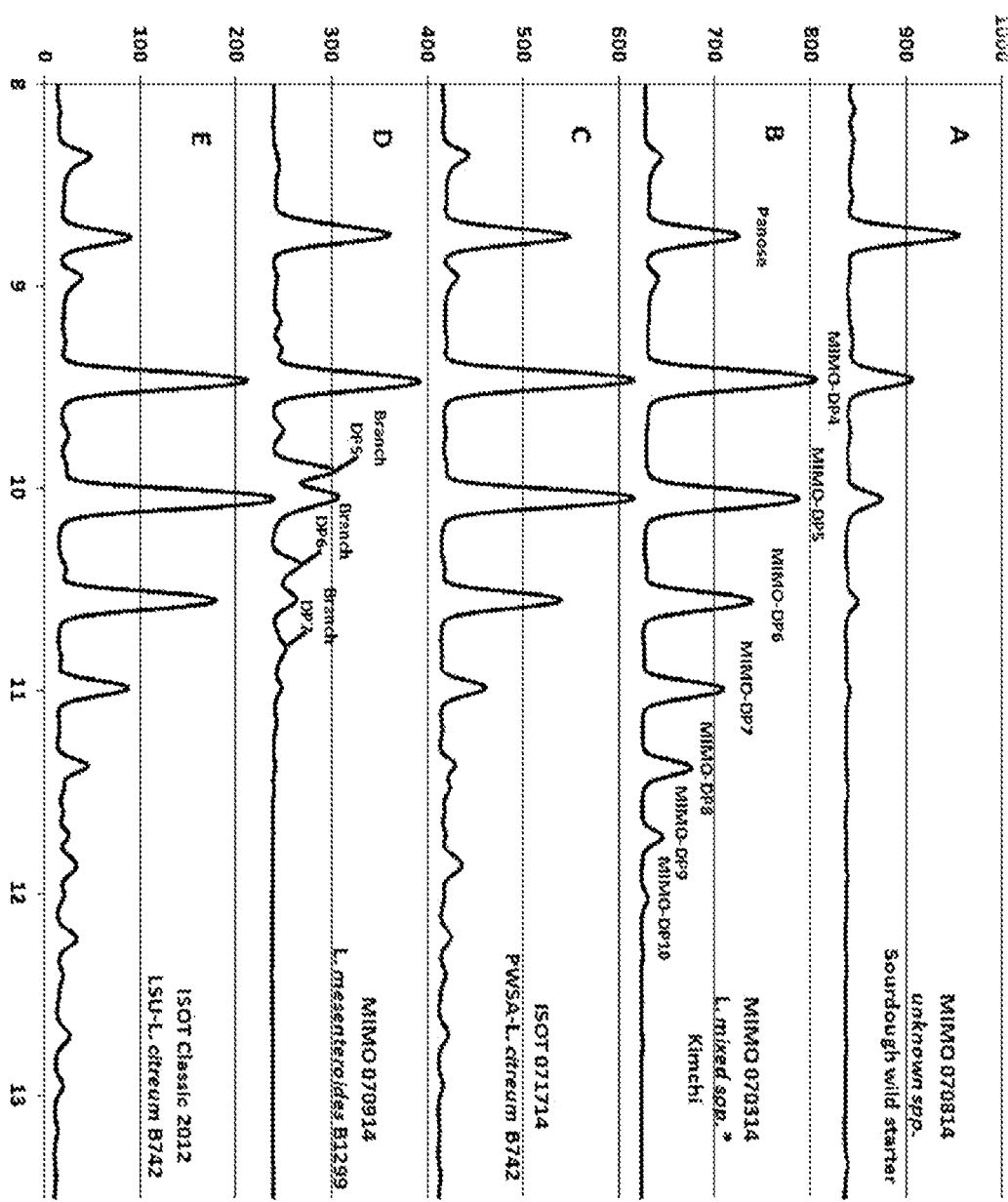
FIG. 9 shows a comparison of fermentations using *Leuconostoc* spp. NRRL B742, 1299, and kimchi as the dextransucrase-producing microorganism; trace A is from sample MIMO 070814 using a species found in sourdough wild starter, which produced a low product concentration that appears to be both linear and branched; trace B is from sample MIMO 070314 using a mixed species of *Leuconostoc* derived from kimchi, which produced a high linear product concentration; trace C is from sample ISOT 071714 using PWSA-*L. citreum* B742, which produced a high product concentration that appears to be linear (DP3-8), with branching at greater DP; trace D is from sample ISOT 070914 using *L. mesenteroides* B1299, which produced a medium product concentration with branching at DP>4; and trace E is from sample ISOT Classic 2012 using *L. citreum* B742, which produced a high product concentration that appears to be linear (DP3-8) with branching at greater DP.

The evaluation of Kimchi by PCR (16ssRNA) as described above demonstrates that fermentation with mixed species of *Leuconostoc* is capable of producing dextransucrase and the desired MIMO product. In addition, species of *Pediococcus*, such as *Pediococcus pentosaceus*, can also produce desirable MIMO product. The data shown in FIG. 9 demonstrates that dextransucrase-producing microorganisms other than *L. mesenteroides* both individually and in mixed cultures may be used in the method of the present invention.

Example 10

Commercial Scale Production

*L. citreum* was purchased from the American Type Culture Collection (ATCC 13146, Manassas, Va.). After re-isolation, the strain was stored in a −74° C. freezer in 20% glycerol. This two-liter culture was grown at 27° C. in a medium composed of sucrose (100 g/L), maltose (50 g/L), yeast extract (5 g/L), $MgSO_4.7H_2O$ (0.2 g/L), $FeSO_4.7H_2O$ (0.01 g/L), NaCl (0.01 g/L), $MnSO_4.7H_2O$ (1.5 g), $CaCl_2$ (0.05 g/L), $KH_2PO_4$ (3 g/L at pH 6.5). Yeast extract (0.075 kg), $MgSO_4$ (1.46 g, anhydrous), $FeSO_4.7H_2O$ (1.5 g), NaCl (0.15 g), $MnSO_4.H_2O$ (20 mg), $CaCl_2$ (0.8 g), and $KH_2PO_4$ (40.00 g) were dissolved in distilled water (12.6 kg) and adjusted to pH 7 using with NaOH (3.2 g, 50%) prior to innoculation. The mixture was autoclaved for 15 min at 120° C. Solutions of maltose.$H_2O$ (0.864 kg) and sucrose (1.910 kg) were sterilized prior to transfer to the fermentor.

At startup, the entire system was flushed, cleaned and sterilized. The fermenter was then charged with maltose, sucrose and nutrients in the quantities given above. The materials were thoroughly mixed. The inoculum is grown to OD-1 (Optical density or absorbance at 660 nm via UV-VIS spectrophotometer).

The fermentation was continued until complete. The inocula cells were removed from contents of the fermenter and discarded. The broth was decolorized as described above.

Example 11

Commercial Scale Production Using Optional De-Ashing and Crystallization Steps

After harvesting, cells are removed by centrifugation at 9-14 k*g for 20 to 30 min. After removal of the cells, the liquor is concentrated to about 35-40 brix prior to treatment with activated charcoal (0.5-3.0% w/w, Carbochem DC-50, or equivalent) to decolorize the liquor. After filtration and washing, the decolorized liquor is about 35 brix. This liquor is put through SAC and WBA chromatography as described above for further purification.

Alternatively, following decolorization, the broth is either put through de-ashing or concentrated to 56-59 brix for crystallization. Crystallization occurs overnight at room temperature. The crystallized mannitol is spun off (~400 g/15 L batch) and the liquor is refrigerated at 5° C. overnight. A second crop of mannitol may then be spun off, producing, for example, about 100 g/15 L per batch). The liquor is then concentrated to 63-65 brix to yield the final IMMO product.

Alternatively, MIMOs may be concentrated to 30-40 brix, then spray dried to yield a powdered product.

Example 12

Production of Maltosyl-Isomaltooligosaccharides (MIMOs)

3,000-Liter Fermenter Scale

The MIMO product prepared in this example was prepared under cGMP and kosher parve conditions. Details of the process that are not specifically mentioned herein are the same as those for Examples 10 and 11. Unless otherwise specified, all equipment was cleaned in place before being utilized or re-utilized in the process steps. Care was taken to sanitize all equipment and transfer lines and hoses in accordance with cGMP standards in the biofermentation industry for products for human consumption.

Samples were taken throughout the fermentation and purification process for continuous QC monitoring as summarized in Table 5.

TABLE 5

| Analysis Performed | Shake Flasks | Seed Fermenter | Formulation Batch Phase; T = 0-24 hrs | Formulation Hold Phase; T = 24-55 hrs |
|---|---|---|---|---|
| $OD_{600}$ | Final | Every 4 hours | Every 4 hours | Every 4 hours |
| pH | Final | Every 2 hours | Every 2 hours | Every 2 hours |
| Micro exam | Final | Final | Every 8 hours | Every 8 hours |
| Brix measurement** | X | Final | Every 8 hours | Every 8 hours + Final |
| Retained QA samples | Final | Final | Every 2 hours | Every 2 hours + Final |

**Brix measurements were taken by a hand-held device.

The following reagents and starting materials were dissolved in 3.7 liters RO water (3.7 liters): potassium phosphate monobasic (0.0118 Kg), anhydrous magnesium sulfate (0.000431 Kg), ferrous sulfate heptahydrate (0.000045 Kg), manganese sulfate monohydrate (0.000045 Kg), sodium chloride (0.000045 Kg), and calcium chloride dihydrate USP (0.00024 Kg), yeast extract (bacteriological grade; 0.0221 Kg), sucrose (Pure Cane Extra Fine Granulated Sugar; 0.53021 Kg); maltose (Sunmalt-S[N] maltose monohydrate; 0.2935 Kg). The initial pH was adjusted to 7.0 using 50% sodium hydroxide FCC (0.005 Kg). This medium was divided into six Fernbach flasks, plugged, autoclaved at 121° C. for 15 minutes, and then cooled to room temperature.

*L. citreum* (B-742; ATCC 13146), previously preserved as 1.0 ml aliquots of a 1:1 w/w broth/glycerol mixture), were thawed at room temperature. Five flasks were aseptically inoculated with 1.0 ml of the prepared *L. citreum*. The sixth flask served as an uninoculated control. All flasks were shaken at 27° C. at 150 rpm overnight (16 hours) until the optical density (OD) was ≥1. The $OD_{600}$ of a sample from each flask was measured on a Shimadzu spectrophotometer. A microscopic examination of a sample from each flask was also conducted to look for growth of the *L. citreum* and to rule out contamination. The healthy cultures from the five flasks were aseptically transferred to a sterile, 2-gallon pressure vessel.

To produce the sugar and salt stock solution, a 1200-gallon fermenter was charged with 1440 Kg RO water, sucrose (Pure Cane Extra Fine Granulated Sugar; 498.96 Kg); maltose (Sunmalt-S[N] maltose monohydrate; 200.0 Kg), sodium chloride (0.037 Kg), and calcium chloride hydrate USP (0.204 Kg). The mixture was thoroughly stirred before transferring by sterile filtration to seed and stock production tanks.

A 300-gallon seed fermenter fitted with two pH probes and an air sparger was prepared for fermentation by mixing 238 Kg RO water, 2.76 Kg yeast extract (bacteriological grade), 1.48 Kg potassium phosphate monobasic, 54.2 grams anhydrous magnesium sulfate, 5.7 grams ferrous sulfate heptahydrate, and 5.7 grams manganese sulfate monohydrate.

The sugar and salt stock solution (309.2 Kg) was aseptically transferred to the seed fermenter via filter sterilization. Immediately after the transfer, 10 Kg RO water was added to a 15-gallon pressure vessel, the vessel pressurized and the water aseptically filter sterilized into the seed tank. An additional 20 Kg RO water was added to adjust the brix of the fermentation mixture.

The seed tank was inoculated with the healthy combined cultures via aseptic lines. The pH of the tank was recorded. Fermentation was allowed to occur without pH adjustment for 16 hours at 27.0° C.±1.0 and aeration. The pH was monitored every 2 hours and the $OD_{600}$ measured every four hours.

The 1200-gallon fermentation tank was then charged with 1332 Kg RO water, 15.01 Kg yeast extract (bacteriological grade), 8.01 Kg potassium phosphate monobasic, 292.2 grams anhydrous magnesium sulfate, 30.0 grams ferrous sulfate heptahydrate, and 30.0 grams manganese sulfate monohydrate. The mixture was stirred at 50 rpm to dissolve the dry ingredients. The pH was recorded at 5.70, but not adjusted. The tank was held at 37° C. for two additional hours while making certain that the air sparger continued to function properly.

The media was then sterilized at 121° C. for 60 minutes. The tank was cooled to 27° C. via slight aeration through the sparger line. The previously prepared sugar and salt stock solution was aseptically transferred (1676.1 Kg) via filter sterilization. The initial pH was 5.71. The previously prepared seed solution (31.0 Kg) was aseptically transferred to the production fermenter. The air supply to the headspace was turned on. The pH was again measured and adjusted to approximately 7.0 using 50% sodium hydroxide solution.

Fermentation was allowed to continue in the tank at 27° C.±1.0, with head space aeration and agitation. The pH was maintained at 5.5±0.05 using 50% sodium hydroxide solution. The $OD_{600}$, brix, and microbiological inspection were monitored as given in Table 5. The fermentation was allowed to continue until complete and fructose was not detectable. The fermentation tank was then cooled to 10° C.

The spent *L. citreum* bacterial cells were removed from the fermentation broth via microfiltration, followed by six stages of diafiltration at an inlet pressure of up to 20 psi. Briefly, the fermentation broth was pressure filtered through microfiltration membranes to ensure removal of as much cellular debris as possible. The cellular material retained by the microfilters was washed with 750 Kg RO water six times to enhance product recovery and yield. The aqueous permeates were combined for concentration and de-colorization.

The product mixture was concentrated using a heated wiped film evaporator. Periodically, the concentrated product mixture was sampled and the brix level determined via a hand-held meter. Concentration was discontinued when the brix level reached 40.

The concentrated fermentation broth was de-colorized using powdered activated carbon (26.25 Kg, CA-50S). The product mixture was heated to 65° C. and the carbon was added along with Celite© 545 (21.0 Kg). The resulting slurry was stirred for about 30 minutes before reducing the temperature to 50° C. The activated carbon was removed by pressing the product mixture through a Sperry filter press that was pre-coated with more Celite 545 (21.0 kg) suspended in 300 Kg RO water. The product mixture was then recirculated through the pre-coated filter press until the filtrate was clear. Finally, it was pumped through a 1 micron polishing filter. Additional MIMO product was recovered by washing the Sperry filter press by adding 250 Kg RO water, agitating the tank contents and then recirculating through the filter press until the filtrate was clear. Again, this filtrate was pumped through a 1 micron polishing filter.

In appropriately sized batches (1350 L at 40 brix total, 6 stages of 225 L feed each for a total of six feed/regeneration cycles), ion exchange chromatography (IEX) is utilized to remove ash (comprised of minerals not consumed during the fermentation process), residual colored organic compounds, organic acids, proteins and amino acids. The resulting combined product is evaporated to a concentration of 56 brix. The product is then cooled to room temperature while agitating to facilitate crystallization of any remaining mannitol. The mannitol crystals are removed by basket centrifugation or by filtering out the crystalline mannitol crystals. The crystals are washed with cold water to remove the product, which is retained for future use. The product is evaporated to a concentration of 65 brix.

The product mixture is again cooled to room temperature while agitating to facilitate crystallization of any remaining mannitol. The product mixture is further cooled to 4° C. with agitation to facilitate crystallization of any remaining mannitol. Any resulting crystalline mannitol is removed by basket centrifuge or by filtration of the final product and the crystals again washed with cold RO water to recover any remaining MIMO product. The wash water is retained for future use. The final product is a clear, colorless, slightly viscous liquid.

Example 13

Improvements in Yield by Fermentation at Higher Total Sugars

Typically, fermentation production processes for MIMOs are not run at high total solids in order to avoid issues related to osmotic shock of the working organism. Previous work (12 full batches at 15.5 kg) indicated that fermentation at approximately 17.6% total sugar gives the proper product distribution, yield, and is reproducible. Thus, increasing the total sugar (TS) content should increase product yield. Here, 44% is given as overall product recovered at pilot scale, not yield in the production-scale fermenter, which is typically 56-58%. The TS can be thus increased until the organism either loses productivity or begins to reject its condition, metabolically, in order to protect itself, e.g. by the production glycerol or ethanol, which are undesirable contaminants in a final product. A second limitation on osmotic strength is the resistance of the enzyme to deformation from its preferentially active conformation due to insufficient hydration and/or co-substrate (e.g. water, in the case of hydrolytic enzymes).

In order to attempt to span a reasonable range of working concentrations, a two-kilogram fermentation was run at a sucrose:maltose ratio of 2.75:1 and at a TS of 30%. The fermentation behaved identically at 30% TS to the established method fermenting 17.6%. The yield, purity, and product distribution were identical once normalized over the total refractive dry solids (RDS). For yield calculations, the % w/w and derived values are given below in Table 6 and Table 7.

TABLE 6

| Analytics % w/w | 3000 kg 37 Hr A | 2 kg 30Bx #1 |
|---|---|---|
| Brix | 18.3 | 29.2 |
| mannitol | 4.885 | 7.400 |
| glucose | 0.007 | 0.057 |
| fructose | 0.011 | 0.002 |
| sucrose | 0.825 | 0.317 |
| maltose | 0.315 | 0.806 |
| panose | 1.370 | 2.383 |
| MIMO-DP4 | 3.469 | 5.470 |
| MIMO-DP5 | 3.431 | 5.423 |
| MIMO-DP6 | 1.488 | 2.573 |
| MIMO-DP7 | 0.435 | 0.777 |
| MIMO-DP8 | 0.186 | 0.324 |
| MIMO-DP9 | 0.000 | 0.000 |
| MIMO-DP10 | 0.000 | 0.000 |
| Lactate | 2.137 | 3.061 |
| Glycerol | 0.027 | 0.060 |
| Formate | 0.000 | 0.000 |
| Acetate | 0.899 | 1.420 |
| Ethanol | 0.097 | 0.153 |

TABLE 7

| | 3000 kg | 2.005 kg |
|---|---|---|
| Fermented amount | | |
| Sucrose, kg | 388.8 | 0.420 |
| Maltose, kg | 156.5 | 0.169 |
| Total, kg | 3072.3 | 2.005 |
| Totals | | |
| MIMO, % | 10.38 | 16.95 |
| TOTAL, % | 19.58 | 30.23 |
| Purity, % | 53.00 | 56.08 |
| Yields | | |
| TS, % | 17.7 | 29.4 |
| TS, kg | 545.2 | 0.589 |
| ISOT, kg | 318.9 | 0.340 |
| yield, % | 58.48 | 57.71 |
| MWD, Da | 763.77 | 759.06 |
| ISOT kg@3000 | 318.85 | 542.50 |
| @ 44% | 239.90 | 397.05 |

These data show that the yields of a 3000-Kg batch at 17.7% TS are not significantly different from the 2-Kg batch fermented at 29.4% TS, 58.48 vs. 57.71%, respectively. Mass-average molecular weight distribution (MWD) was likewise similar at 763.77 vs 759.06 Da (target 760 Da) for TS fermented at 17.7% and 29.4%, respectively. Further, the increase in TS did increase yield from 318.85 kg to a calculated 542.5 Kg/batch improving the recoverable yield by, in the worst case 49.28% and in the best case, 70.14%.

Example 14

Removal of Mannitol Via Crystallization from the MIMOs

As described in Example 12, the MIMO product can be further processed at the end of the described process to remove any remaining mannitol to further improve the purity of the final product. This example describes improvements to the process of removing mannitol via crystallization.

In one method, IEX product ("IEX out" in Table 8) was evaporated to 56° brix and was allowed to crystallize ("XL #1") at room temperature. The mannitol crystals were removed (cake #1) via either a basket centrifuge fitted with a polypropylene filter bag with 10 µm pores or a nutsch pressure filter with 10 µm equivalent plate/screen. The cake was washed with 500 mL cold water (appx. 125% cake w/w) and the washings were collected for recycle ("wash #1"). The resulting liquor ("liquor #1") was cooled to 2-5° C. and was allowed to crystallize ("XL #2"). The mannitol crystals were removed ("cake #2") via either a basket centrifuge fitted with a polypropylene filter bag with 10 µm pores or a nutsch pressure filter with 10 µm equivalent plate/screen. The cake was washed with 500 mL cold water (approximately 125% cake w/w) and the washings were collected for recycle ("wash #2"). The crystals are removed as before, and the resulting liquor is sent to final concentration to a product brix of 63-64°. Table 8 shows a typical mass balance, given as the averages from 11 batches.

TABLE 8

| | Stage | | | | | | | | | |
|---|---|---|---|---|---|---|---|---|---|---|
| | IEX | | | XL #1 | | | XL #2 | | | |
| Values | IEX in | IEX out | Evap 2 | Liquor #1 | Wash #1 | Cake #1 | Liquor #2 | Wash #2 | Cake #2 | Recycle |
| kg | 7.290 | 26.839 | 3.265 | 2.548 | 0.647 | 0.402 | 2.425 | 0.612 | 0.114 | 1.259 |
| Brix | 35.46 | 8.03 | 57.36 | 52.82 | 19.79 | 89.59 | 50.51 | 13.64 | 89.26 | 16.72 |
| RDS, kg | 2.48 | 1.81 | 1.87 | 1.346 | 0.13 | 0.317 | 1.225 | 0.08 | 0.087 | 0.21 |
| Ash, kg | 0.032 | 0.000 | 0.000 | 0.000 | 0.000 | 0.000 | 0.000 | 0.000 | 0.000 | 0.000 |
| ISOT, kg | 1.097 | 1.064 | 1.064 | 0.988 | 0.09 | 0.031 | 0.939 | 0.07 | 0.010 | 0.16 |
| Acids, kg | 0.517 | 0.000 | 0.000 | 0.000 | 0.000 | 0.000 | 0.000 | 0.000 | 0.000 | 0.000 |
| Mannitol, kg | 0.698 | 0.677 | 0.677 | 0.360 | 0.03 | 0.317 | 0.230 | 0.02 | 0.087 | 0.05 |

TABLE 8-continued

| | Stage | | | | | | | | | |
|---|---|---|---|---|---|---|---|---|---|---|
| | IEX | | | XL #1 | | | XL #2 | | | |
| Values | IEX in | IEX out | Evap 2 | Liquor #1 | Wash #1 | Cake #1 | Liquor #2 | Wash #2 | Cake #2 | Recycle |
| Solids, kg | 2.34 | 1.74 | 1.74 | 1.35 | 0.13 | 0.35 | 1.17 | 0.08 | 0.10 | 0.21 |
| Purity, % | 46.77 | 61.10 | 61.10 | 73.28 | 73.28 | 8.82 | 80.33 | 80.33 | 10.16 | 76.06 |

In an improved method, IEX product ("IEX out") was evaporated to 56° brix and was allowed to crystallize (XL #1) at room temperature. The mannitol crystals were removed ("cake #1") via either a basket centrifuge fitted with a polypropylene filter bag with 10 μm pores or a nutsch pressure filter with 10 μm equivalent plate/screen. The cake is washed with 500 mL cold water (appx. 125% cake w/w) and the washings collected for recycle ("wash #1"). The resulting liquor ("liquor #1") was allowed to crystallize ("XL #2") at room temperature. Once cooled and crystallization was observed, the entire mixture was cooled to 2-5° C. and was allowed to crystallize until complete. The mannitol crystals were removed ("cake #2") via either a basket centrifuge fitted with a polypropylene filter bag with 10 μm pores or a nutsch pressure filter with 10 μm equivalent plate/screen. The cake was washed with 500 mL cold water (approximately 125% cake w/w) and the washings were collected for recycle ("wash #2"). The data from this experiment are shown below in Table 8. The product has a brix of 63-64° brix and was ready for pasteurization and packaging as commercial material.

TABLE 8

| | Stage | | | | | | | | | | |
|---|---|---|---|---|---|---|---|---|---|---|---|
| | EX | | | XL #1 | | | | XL #2 | | | |
| Values | IEX in | IEX out | Evap 2 | Liquor #1 | Wash #1 | Cake #1 | Evap 3 | Liquor #2 | Wash #2 | Cake #2 | Recycle |
| kg | 7.027 | 29.747 | 2.908 | 2.46 | 0.632 | 0.354 | 1.916 | 1.545 | 0.481 | 0.120 | 1.113 |
| Brix | 32.20 | 5.86 | 57.01 | 51.29 | 14.90 | 93.58 | 65.85 | 63.45 | 21.40 | 92.16 | 17.71 |
| RDS, kg | 2.26 | 1.74 | 1.73 | 1.26 | 0.09 | 0.33 | 1.26 | 0.98 | 0.10 | 0.11 | 0.200 |
| Ash, kg | 0.157 | 0.000 | 0.000 | 0.000 | 0.000 | 0.000 | 0.000 | 0.000 | 0.000 | 0.000 | 0.000 |
| ISOT, kg | 1.199 | 1.137 | 1.137 | 1.058 | 0.040 | 0.003 | 1.058 | 0.892 | 0.067 | 0.002 | 0.107 |
| Acids, kg | 0.363 | 0.000 | 0.000 | 0.000 | 0.000 | 0.000 | 0.000 | 0.000 | 0.000 | 0.000 | 0.000 |
| Mannitol, kg | 0.595 | 0.569 | 0.569 | 0.218 | 0.049 | 0.259 | 0.218 | 0.066 | 0.032 | 0.081 | 0.081 |
| Solids, kg | 2.31 | 1.71 | 1.71 | 1.28 | 0.09 | 0.26 | 1.28 | 0.96 | 0.10 | 0.08 | 0.19 |
| Purity, % | 53.70 | 64.26 | 64.26 | 78.63 | 43.74 | 1.14 | 78.63 | 87.59 | 64.85 | 2.53 | 57.07 |

Alternatively, after purifying the product mixture using IEX as described above, the product mixture is evaporated to 56 brix, then cooled to room temperature while stirring to encourage crystal formation of the mannitol present. After about 12 to about 16 hours, the crystals are removed via basket centrifugation, or by utilizing a vibrating screen filter, or by using a nutsch filter, or by using combinations of these techniques which are well known to one skilled in the art. The remaining liquid is evaporated to 65-66 brix, then cooled to room temperature while stirring to encourage crystal formation for 12 to 16 hours. The mixture is cooled to 4° C. to encourage crystallization of any remaining mannitol. A two-stage crystallization process, i.e., one using two different temperatures, is necessary in order to allow the crystals to form properly. After about 12 to about 16 hours, the crystals are removed via basket centrifugation, or by utilizing a vibrating screen filter, or by using a nutsch filter, or by using combinations of these techniques. The product is now ready for pasteurization and packaging as commercial material.

All publications and patent applications mentioned in this specification are herein incorporated by reference to the same extent as if each individual publication or patent application were specifically and individually indicated to be incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for the preparation of oligosaccharides comprising:
 (a) contacting a feedstock comprising sucrose and maltose having at least a 2.33:1 starting ratio of sucrose to maltose with dextransucrase producing bacterial cells in an aqueous culture medium, where the dextransucrase is of enzyme classification (EC) 2.4.1.5;
 (b) fermenting the feedstock with the bacterial cells while controlling the culture medium at a pH between 4 and 6.0 by adding an acid or a base to the culture medium;
 (c) removing the bacterial cells to produce a fermentation broth; and
 (d) polishing the fermentation broth to produce a final composition;
 wherein the final composition of the oligosaccharides comprises maltosyl-isomaltooligosaccharides with degrees of polymerization greater than 2 (DP2).

2. The method of claim 1, wherein performing steps (a) to (c) is continuous.

3. The method of claim 1, wherein the method is conducted as an immobilized cell process.

4. The method of claim 1, wherein the method is conducted as a batch or a fed-batch operation.

5. The method of claim 1, wherein the starting ratio of sucrose to maltose ranges up to 7:1.

6. The method of claim 1, wherein the starting ratio is 2.33:1; 3.17:1; 3.2:1; or 2.75:1.

7. The method of claim 1, wherein the ratio of sucrose to maltose is adjusted during the fermentation process by the addition of either more sucrose or more maltose.

8. The method of claim 1, wherein the dextransucrase-producing bacterial cells are *Leuconostoc mesenteroides, Leuconostoc citreum, Leuconostoc gasicomitatum,* or *Leuconostoc kimchii*.

9. The method of claim 8, wherein the dextransucrase-producing bacterial cells are *Leuconostoc citreum* ATCC 13146 or *Leuconostoc citreum* NRRL B-742 or *Leuconostoc mesenteroides* subsp. *mesenteroides* NRRL B-1299.

10. The method of claim 1, wherein the dextransucrase-producing bacterial cells are *Weisella confusa, Weisella cibaria, Lactococcus* spp, *Pediococcus* spp, *Pediococcus pentosaceus, Streptococcus mutans, Streptococcus oralis, Streptococcus sanguinis, Lactobacillis* spp, or *Lactobacillis reuteri*.

11. The method of claim 1, wherein the base comprises an alkali earth metal hydroxide or carbonate.

12. The method of claim 1, wherein the bacterial cells are removed by centrifugation, filtration or clarification.

13. The method of claim 1, wherein the polishing removes insoluble impurities or comprises decolorization or comprises de-ashing or comprises removing protein or comprises removing organic acids or comprises combinations of these steps.

14. The method of claim 13, wherein the decolorization utilizes activated charcoal or activated carbon or comprises using a weak base anion resin or comprises a combination of these steps.

15. The method of claim 13, wherein the de-ashing comprises using a strong acid cation resin to remove metal ions.

16. The method of claim 13, wherein the de-ashing comprises a two-step process using a strong acid cation resin followed by a weak base anion resin.

17. The method of claim 13, wherein the removing protein comprises heating, evaporation, centrifugation, filtration, using activated carbon, using a weak base anion resin, or a combination thereof.

18. The method of claim 13, wherein the removing the organic acids utilizes a chromatographic grade gel-type strong acid cation exchange resin in calcium form (SAC-Ca++).

19. The method of claim 13, wherein the removing organic acids comprises utilizing a weak base anion resin.

20. The method of claim 1, wherein the final composition of the oligosaccharides produced comprises isomaltooligosaccharides with an $\alpha$-(1>4) linkage at the reducing end and $\alpha$-(1→6) linkages with a degree of polymerization between 3 and 10 or between 3 and 9.

21. The method of claim 20, wherein the isomaltooligosaccharides further comprise $\alpha$-(1→4), $\alpha$-(1→3) and/or $\alpha$-(1→2) branching.

22. The method of claim 1, further comprising providing the oligosaccharides as a concentrated solution.

23. The method of claim 1, further comprising providing the oligosaccharides as a powder produced by drying or by spray drying or by freeze drying.

24. The method of claim 1, wherein the aqueous culture medium comprises a filter sterilized sugar and salt stock solution.

* * * * *

UNITED STATES PATENT AND TRADEMARK OFFICE
CERTIFICATE OF CORRECTION

PATENT NO. : 11,155,847 B2
APPLICATION NO. : 15/505536
DATED : October 26, 2021
INVENTOR(S) : Madsen, II et al.

Page 1 of 1

It is certified that error appears in the above-identified patent and that said Letters Patent is hereby corrected as shown below:

On the Title Page

In item (71), in "Applicants", in Column 1, Lines 1-5, delete "Applicants: ISOThrive LLC, Healdsburg, CA (US); Board of Supervisors of Louisiana State University and Agricultural and Mechanical College, Baton Rouge, LA (US)" and insert --Applicant: ISOThrive Inc., Healdsburg, CA (US)-- therefor In the Claims In Column 31, Line 20, in Claim 9, after "*mesenteroides*", delete "subsp. *mesenteroides*"

In Column 32, Line 22, in Claim 20, delete "α-(1>4)" and insert --α-(1→4)-- therefor Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*